(12) United States Patent
Yokoyama et al.

(10) Patent No.: US 8,226,976 B2
(45) Date of Patent: Jul. 24, 2012

(54) METHOD OF USING CELL-FREE PROTEIN SYNTHESIS TO PRODUCE A MEMBRANE PROTEIN

(75) Inventors: Shigeyuki Yokoyama, Kanagawa (JP); Kazumi Shimono, Kanagawa (JP); Mikako Shirouzu, Kanagawa (JP); Mie Goto, Kanagawa (JP)

(73) Assignee: Riken, Wako-shi, Saitama (JP)

( * ) Notice: Subject to any disclaimer, the term of this patent is extended or adjusted under 35 U.S.C. 154(b) by 0 days.

(21) Appl. No.: 12/741,575

(22) PCT Filed: Nov. 5, 2008

(86) PCT No.: PCT/JP2008/070116
§ 371 (c)(1),
(2), (4) Date: Jul. 9, 2010

(87) PCT Pub. No.: WO2009/060857
PCT Pub. Date: May 14, 2009

(65) Prior Publication Data
US 2010/0291189 A1  Nov. 18, 2010

(30) Foreign Application Priority Data
Nov. 5, 2007 (JP) .................................. 2007-286899

(51) Int. Cl.
*A61K 9/127* (2006.01)
*A61K 38/00* (2006.01)
*G01N 33/00* (2006.01)
*C07K 1/00* (2006.01)
*C07K 2/00* (2006.01)
*C07K 4/00* (2006.01)
*C07K 5/00* (2006.01)
*C07K 7/00* (2006.01)
*C07K 14/00* (2006.01)
*C07K 16/00* (2006.01)
*C07K 17/00* (2006.01)

(52) U.S. Cl. ........... 424/450; 436/86; 530/300; 530/350

(58) Field of Classification Search .................. None
See application file for complete search history.

(56) References Cited

U.S. PATENT DOCUMENTS

| | | | |
|---|---|---|---|
| 5,264,341 A | 11/1993 | Maciak et al. | |
| 5,270,181 A | 12/1993 | McCoy et al. | |
| 5,532,151 A | 7/1996 | Chantry et al. | |
| 5,674,729 A | 10/1997 | Wimmer et al. | |
| 5,800,984 A | 9/1998 | Vary | |
| 5,804,374 A | 9/1998 | Baltimore et al. | |
| 5,869,286 A | 2/1999 | Yao et al. | |
| 5,959,085 A | 9/1999 | Garrone et al. | |
| 5,962,246 A | 10/1999 | Ladner et al. | |
| 6,136,568 A | 10/2000 | Hiatt et al. | |
| 6,303,337 B1 | 10/2001 | Rothschild et al. | |
| 6,511,832 B1 | 1/2003 | Guarino et al. | |
| 6,780,607 B2 | 8/2004 | Choi et al. | |
| 7,045,593 B2 * | 5/2006 | Tajima et al. ................. | 530/333 |
| 7,195,895 B2 | 3/2007 | Motoda et al. | |
| 7,253,144 B2 * | 8/2007 | Shirouzu et al. ............. | 435/69.1 |
| 7,348,134 B2 | 3/2008 | Lingappa et al. | |
| 2002/0025525 A1 | 2/2002 | Shuber | |
| 2002/0142387 A1 | 10/2002 | Seki et al. | |
| 2003/0050453 A1 | 3/2003 | Sorge | |
| 2004/0121346 A1 | 6/2004 | Endo et al. | |
| 2004/0137448 A1 | 7/2004 | Thornton et al. | |
| 2005/0095705 A1 | 5/2005 | Kadan et al. | |
| 2005/0244920 A1 | 11/2005 | Shirouzu et al. | |
| 2007/0281337 A1 | 12/2007 | Imataka et al. | |

FOREIGN PATENT DOCUMENTS

| | | |
|---|---|---|
| EP | 0469610 A1 | 2/1992 |
| EP | 1143009 A1 | 10/2001 |
| EP | 1176210 A1 | 1/2002 |
| EP | 1316616 A1 | 6/2003 |
| EP | 1354959 A1 | 10/2003 |
| EP | 1384778 A1 | 1/2004 |
| EP | 1507003 A1 | 2/2005 |
| EP | 1857558 A1 | 11/2007 |
| JP | 4-200390 A | 7/1992 |
| JP | 7-110236 A | 4/1995 |
| JP | 9-107954 A | 4/1997 |
| JP | 9-234074 A | 9/1997 |
| JP | 2000-175695 A | 6/2000 |
| JP | 2000-325076 A | 11/2000 |
| JP | 2002-238595 A | 8/2002 |
| JP | 2003018999 A | 1/2003 |
| JP | 2003-235598 A | 8/2003 |

(Continued)

OTHER PUBLICATIONS

Giuliodori et al., "Preferential translation of cold-shock mRNAs during cold adaptation", RNA, vol. 10, pp. 265-276, 2004. Nishimura et al., "Cell-Free System Derived from Heat-Shocked *Escherichia coli*: Synthesis of Enzyme Protein Possessing Higher Specific Activity", Journal of Fermentation and Bioengineering, vol. 79, No. 2, pp. 131-135, 1995.
Yu et al., "An efficient recombination system for chromosome engineering in *Escherichia coli*", PNAS, vol. 97, No. 11, pp. 5978-5983, 2000.
Rowen et al., NCBI Protein AAF 02829, Submitted Apr. 25, 1999, Multimegabase Sequenceing Center, University of Washington.
Zubay, G., "In vitro synthesis of protein in microbial systems", Annual Review of Genetics, vol. 7, pp. 267-287, 1973.
Pratt et al., "Identification of gene products programmed by restriction endonuclease DNA fragments using an *E. coli* in vitro system", Nucleic Acids Research, vol. 9, No. 18, pp. 4459-4474, 1981.
Benzinger et al., "Transfection of *Escherichia coli* Spheroplasts", Journal of Virology, vol. 15, No. 4, pp. 861-871, 1975.
Lorenz et al., "Bacterial Gene Transfer by Natural Genetic Transformation in the Environment", Microbiological Reviews, vol. 58, No. 3, pp. 563-602, 1994.
Yang et al., "Cell-free coupled transcription-translation system for investigation of linear DNA segments", Proc. Natl. Acad. Sci., vol. 77, No. 12, pp. 7029-7033, 1980.
Office Action mailed Sep. 14, 2010 in Japanese Application No. 2004-335514.

(Continued)

*Primary Examiner* — Robert Landsman
(74) *Attorney, Agent, or Firm* — Birch, Stewart, Kolasch & Birch, LLP

(57) ABSTRACT

A method is provided for producing a membrane protein folded to its native structure or active structure in a lipid disc or a liposome. The method comprises: (a) preparing a reaction solution for cell-free protein synthesis containing a polynucleotide encoding a membrane protein, a steroidal detergent, and a phospholipid, wherein the steroidal detergent is contained at a concentration higher than its critical micelle concentration; (b) decreasing the concentration of said steroidal detergent in the reaction solution; and (c) synthesizing the membrane protein simultaneously with formation of a lipid disk or liposome into which the synthesized membrane protein is integrated.

10 Claims, 10 Drawing Sheets

FOREIGN PATENT DOCUMENTS

| | | |
|---|---|---|
| JP | 2004-91790 A | 3/2004 |
| JP | 2004-215651 A | 8/2004 |
| JP | 2004-267205 A | 9/2004 |
| JP | 2004-290181 A | 10/2004 |
| JP | 2005-6646 A | 1/2005 |
| JP | 2005225796 A | 8/2005 |
| WO | WO-88/08453 A1 | 11/1988 |
| WO | WO-92/07949 A1 | 5/1992 |
| WO | WO-92/11390 A1 | 7/1992 |
| WO | WO-92/13955 A1 | 8/1992 |
| WO | WO-97/46696 A1 | 12/1997 |
| WO | WO-99/02671 A1 | 1/1999 |
| WO | WO-99/14370 A1 | 3/1999 |
| WO | WO-99/20798 A1 | 4/1999 |
| WO | WO-99/57992 A1 | 11/1999 |
| WO | WO-00/56914 A1 | 9/2000 |
| WO | WO-01/83805 A2 | 11/2001 |
| WO | WO-02/18586 A1 | 3/2002 |
| WO | WO-02/090537 A1 | 11/2002 |
| WO | WO-03/097829 A1 | 11/2003 |

OTHER PUBLICATIONS

Wieder K. J. et al., Proceedings of the National Academy of Sciences of USA, 1982, vol. 79, pp. 3599-3603.

Abstract of Mikami S. et al., Protein Expression and Purification, Oct. 25, 2005.

Sawasaki T. et al, "In vitro protein synthesis system: Cell-free protein synthesis system prepared from wheat germ", Protein, Nucleic Acid and Enzyme, vol. 49, No. 11, pp. 1514-1519, 2004.

Pain et al., "Analysis of Translational Activity of Extracts Derived from Oocytes and Eggs of *Xenopus laevis*", Methods in Molecular Biology, vol. 77, pp. 194-209, 1998, XP008075553.

Giller et al., "A homologous in vitro system to analyze transcription of a mouse immunoglobulin u heavg-chain gene", Eur. J. Biochem., vol. 172, pp. 679-685, 1988.

Nishimura et al., "Enhancement of Protein Synthesis in Continuous-Flow, Cell-Free System by Improvement of Membrane Permeation", Journal of Fermentation and Bioengineering, vol. 80, No. 4, pp. 403-405, 1995.

Bochkareva et al, "Chaperonin-promoted Post-translational Membrane Insertion of a Multispanning Membrane Protein Lactose Permease", Journal of Biological Chemistry, vol. 271, No. 36, pp. 22256-22261, 1996.

Wheatley et al., "Glycosylation of G-protein-coupled receptors for hormones central to normal reproductive functioning: its occurrence and role", Human Reproduction Update, vol. 5, No. 4, pp. 356-364, 1999.

Kigawa et al., "Cell-free production and stable-isotope labeling of milligram quantities of proteins", FEBS Letters, vol. 442, pp. 15-19, 1999.

Booth et al., Biochemical Society Transactions, vol. 28, Part 3, p. A50, 2000.

Kigawa et al., "High-throughput Cell-free Protein Expression System for Structural Proteomics", Protein, Nucleic Acid and Enzyme, vol. 47, No. 8, pp. 1014-1019, 2002.

Kain et al., "Universal Promoter for Gene Expression Without Cloning: Expression-PCR", BioTechniques, vol. 10, No. 3, pp. 366-368 and 370, 1991, XP000912135.

MacFerrin et al., "Overproduction and dissection of proteins by the expression-cassette polymerase chain reaction", Proc. Natl. Acad. Sci., vol. 87, No. 5, pp. 1937-1941, 1990, XP000268593.

Ohuchi et al., "In vitro method for the generation of protein libraries using PCR amplification of a single DNA molecule and coupled transcription/translation", Nucleic Acids Research, vol. 26, No. 19, pp. 4339-4346, 1998, XP002119037.

Nakano et al., "Efficient Coupled Transcription/Translation from PCR Template by a Hollow-Fiber Membrane Bioreactor", Biotechnology and Bioengineering, vol. 64, No. 2, pp. 194-199, XP001084028, (1999).

Sandhu et al., "Dual Asymmetric PCR: One-Step Construction of Synthetic Genes", BioTechniques, vol. 12, No. 1, pp. 14-16, 1992, XP002134139.

Horton et al., "Engineering hybrid genes without the use of restriction enzymes: gene splicing by overlap extension", Gene, vol. 77, pp. 61-68, 1989, XP002090392.

Liu et al., "Functional characterization of novel human ARFGAP3", FEBS Letters, vol. 490, Nos. 1-2, pp. 79-83, 2001.

Laage et al., "Strategies for Prokaryotic Expression of Eukaryotic Membrane Proteins", Traffic, vol. 2, No. 2, pp. 99-104, 2001.

Yoshida et al., "In Vitro Synthesis of Hyaluronan by a Single Protein Derived from Mouse HAS1 Gene and Characterization of Amino Acid Residues Essential for the Activity", Journal of Biological Chemistry, vol. 275, No. 1, pp. 497-506, 2000.

Lehto et al., "Release of the glycosylphosphatidylinositol-anchored enzyme ecto-5'-nucleotidase by phospholipase C: catalytic activation and modulation by the lipid bilayer", Biochem. Journal, vol. 332, pp. 101-109, 1998.

The pET Expression System, http://www.bio.davidson.edu/Course/Molbio?nolStudents/spring2003/Causey/p-—ET.html, pp. 1-4, 2003.

Tucker et al., "Purification of a rat neurotensin receptor expressed in *Escherichia coli*", Biochem. Journal, vol. 317, pp. 891-899, 1996.

Grisshammer et al., "Expression of a rat neurotensin receptor in *Escherichia coli*", Biochem. Journal, vol. 295, pp. 571-576, 1993.

Abduiaev et al., "Functionally Discrete Mimics of Light-activated Rhodopsin Identified through Expression of Soluble Cytoplasmic Domains", Journal of Biological Chemistry, vol. 275, No. 50, pp. 39354-39363, 2000.

Sachdev et al., "Solubility of Proteins Isolated from Inclusion Bodies is Enhanced by Fusion to Maltose-Binding Protein or Thioredoxin", Protein Expression and Purification, vol. 12, No. 1, pp. 122-132, 1998.

McIntyre et al., "Procathepsins L and D are Membrane-Bound in Acidic Microsomal Vesicles", Journal of Biological Chemistry, vol. 266, No, 23, pp. 15438-15445, 1991.

Invitrogen, "Flexible in vitro expression with high-yield results", Expressions, vol. 9, Issue 2, p. 7, 2002.

Novagen, "pET-23a-d(+) Vectors", p. 1, 1998.

Falk, "Cell-free synthesis and assembly of connexins into functional gap junction membrane channels", EMBO Journal, vol. 16, No. 10, pp. 2703-2716, 1997.

Rhee et al., "Channel-Forming Activity of Immunoaffinity-Purified Connexin32 in Single Phospholipid Membranes", Biochemistry, vol. 35, No. 28, pp. 9212-9223, 1996.

Ohtaki et al., "Expression, Purification, and Reconstitution of Receptor for Pituitary Adenylate Cyclase-activating Polypeptide", Journal of Biological Chemistry, vol. 273, No. 5, 15464-15473, 1998.

Mambetisaeva et al., "Expression of Three Functional Domains of Connexin 32 as Thioredoxin Fusion Proteins in *Escherichia coli* and Generation of Antibodies", Protein Expression and Purification, vol. 11, No. 1, pp. 26-34, 1997.

Peng et al., "Cystic fibrosis transmembrane conductance regulator: expression and helicity of a double membrane-spanning segment", FEBS Letters, vol. 413, No. 1, pp. 29-33, 1998.

Potapov et al., "Correlation between poly(U) misreading and poly(dT) translation efficiency in *E coli* cell-free systems", Biochimie, vol. 72, pp. 345-349, 1990.

Okamoto-Hosoya et al., "An aberrant protein synthesis activity is linked with antibiotic overproduction in *rpsl.* mutants of *Streptomyces coelicolor* A3(2)", Microbiology, vol. 149, pp. 3299-3309, 2003.

Hu et al., "Novel Approach for Improving the Productivity of Antibiotic-Producing Strains by Inducing Combined Resistant Mutations", Applied and Environmental Microbiology, pp. 1885-1892, 2001.

Hosoya et al., "Acquisition of Certain Streptomycin-Resistant (str) Mutations Enhances Antibiotic Production in Bacteria", Antimicrobial Agents and Chemotherapy, vol. 42, pp. 2041-2047, 1998.

Chumpolkulwong et al., "Effects of *Escherichia coli* ribosomal protein S12 mutations on cell-free protein synthesis", Eur. J. Biochem., vol. 271, pp. 1127-1134, 2004.

Hwang, Y.-I., "Mutant 305 ribosomal subunit S12", Database EMBL, Oct. 1, 2002, XP-002353555.

Office Action mailed Jan. 13, 2009 in Japanese Application No. 2002-345597.

Inaoka et al., "Construction of an in Vivo Nonsense Readthrough Assay System and Functional Analysis of Ribosomal Proteins S12, S4, and S5 in *Bacillus subtilis*", Journal of Bacteriology, vol. 183, No. 17, pp. 4958-4963, 2001.

Funatsu et al., "Ribosomal Proteins: Location of Amino-acid Replacements in Protein S12 isolated from *Escherichia coli* Mutants Resistant to Streptomycin", J. Mol. Biol., vol. 68, pp. 547-550, 1972.

Timms et al., "Mutant sequences in the *rpsL* gene of *Escherichia coli* B/r: mechanistic implications for spontaneous and ultraviolet light mutagenesis", Molecular and General Genetics, vol. 232, pp. 89-96, 1992.

Shehata et al., "Effect, of Temperature on the Size of *Escherichia coli* Cells", Journal of Bacteriology, vol. 124, No. 2, pp. 857-862, 1975.

Patterson et al., "Deductive Analysis of a Protein-Synthesis Mutant of *Escherichia coli*", Biochemical Genetics, vol. 8, No. 2, pp. 205-230, 1973.

Klammt et al., "Cell-Free Production of Integral Membrane Proteins on a Preparative Scale", Methods in Molecular Blology, vol. 375, pp. 57-78, 2007.

Mathews et al., "Mammalian Cell-Free Protein Synthesis Directed by Viral Ribonucleic Acid", Eur. J. Biochem. vol. 17, pp. 328-338, 1970.

Zawada at al., "Effects of Genotype and Growth Conditions on Cell-Free Protein Synthesis Systems", Abstracts of Papers of the American Chemical Society, vol. 224, Nos. 1-2, p. BIOT 91, 2002, XP009068071.

Jones et al., "Function of a Relaxed-Like State following Temperature Downshifts in *Escherichia coli*", Journal of Bacteriology, vol. 174, No. 12, pp. 3903-3914, 1992.

Wang et al, "An Optimized Yeast Cell-Free System: Sufficient for Translation of Human Papillomavirus 58 L1 mRNA and Assembly of Virus-like Particles", Journal of Bioscience and Bioengineering, vol. 106, No. 1, pp. 8-15, 2008.

Hofbauer et al., "Preparation of a mRNA-Dependent Cell-Free Translation System from Whole Cells of *Saccharomyces cerevisiae*", Eur. J. Biochem. vol. 122, pp. 199-203, 1982.

Kim et al., "Expression-independent consumption of substrates in cell-free expression system from *Escherichia coli*", Journal of Biotechnology, vol. 84, pp. 27-32, 2000.

Kim et al., "Continuous Cell-Free Protein Synthesis Using Glycolytic Intermediates as Energy Sources", J. Microbiol. Biotechnol., vol. 18, No. 5, pp. 885-888, 2008.

Ertola et al., "Design, Formulation, and Optimization of Media", Bioprocess Technol., vol. 21, pp. 89-137, 1995.

Lee et al., "Statistical Medium Formulation and Process Modeling by Mixture Design of Experiment for Peptide Overexpression in Recombinant *Escherichia coli*", Applied Biochemistry and Biotechnology, vol. 135, pp. 81-100, 2006.

Kigawa, T., "Large-Scale Preparation of Proteins by the Cell-Free Synthesis", Biophysics, vol. 40, No. 6, pp. 391-394, 2000.

Carroll et al., "Preparation of a Cell-Free Translation System with Minimal Loss of Initiation Factor eIF-2/eIF-2B Activity", Analytical Biochemistry, vol. 212, pp. 17-23, 1993.

Henis-Korenblit et al., "The caspase-cleaved DAP5 protein supports internal ribosome entry site-mediated translation of death proteins", PNAS, vol. 99, No. 8, pp. 5400-5405, 2002.

Person et al., "Translation in Micrococcal nuclease-treated cell-free extracts fromehrlich ascites tumor cells", Biochimica et Biophsica Acta., vol. 783, pp. 152-157, 1984.

Pestova et al., "The structure and function of initiation factors in eukaryotic protein synthesis", Cell. Mol. Life Sci., vol. 57, pp. 651-674, 2000.

Preiss et al., "Starting the protein synthesis machine: eukaryotic translation initiation", BioEssays, vol. 25, No. 12, pp. 1201-1211, 2003.

Thoma et al., "A Poly(A) Tail-Responsive in Vitro System for Cap- or IRES-Driven Translation from HeLa Cells", Methods in Molecular Biol., vol. 257, pp. 171-180, 2004, XP002496677.

Morley et al., "A rabbit reticulocyte factor which stimulates protein synthesis in several mammalian cell-free systems", Biochimica et Biophysica Acta, vol. 825, pp. 57-69, 1985.

Bergamini et al., "Picornavirus IRESes and the poly(A) tail jointly promote cap-independent translation in a mammalian cell-free system", RNA, vol. 6, pp. 1781-1790, 2000.

Scheper et al., "Eukaryotic Initiation Factors-4E and -4F Stimulate 5' cap-dependent as Well as Internal Initiation of Protein Synthesis", Journal of Biological Chemistry, vol. 267, No. 11, pp. 7269-7274, 1992.

Scheper et al., "The 5' untranslated region of encephalomyocarditis virus contains a sequence for very efficient binding of eukaryotic initiation factor eIF-2/2B", Biochimica et Biophysica Acta, vol. 1089, pp. 220-226, 1991.

Nevins et al., "Distinct Regulation of Internal Ribosome Entry Site-mediated Translation following Cellular Stress is Medicated by Apoptotic Fragments of eIF4G Translation Initiation Factor Family Members eIF4GI and p97/DAP6/NAT1", Journal of Biological Chemistry, vol. 278, No. 6, pp. 3572-3579, 2003.

Imataka et al., "A newly identified N-terminal amino acid sequence of human eIF4G binds poly(A)-binding protein and functions in poly(A)-dependent translation", EMBO Journal, vol. 17, No. 24, pp. 7480-7489, 1998.

Svitkin et al., "Poly(A)-binding protein interaction with eIF4G stimulates picornavirus IRES-dependent translation", RNA, vol. 7, pp. 1743-1752, 2001.

Imataka et al., "A new translational regulator with homology to eukaryotic translation initiation factor 4G", EMBO Journal, vol. 16, No. 4, pp. 817-825, 1997.

Mikami et al., "An efficient mammalian cell-free translation system supplemented with translation factors", Protein Expression and Purification, vol. 46, pp. 348-357, 2006.

Pelham et al., "An Efficient mRNA-Dependent Translation System from Reticulocyte Lysates", Eur. J. Biochem., vol. 67, pp. 247-256, 1976.

Lee et al., "Enhanced specific antibody productivity of calcium alginate-entrapped hybridoma is cell line-specific", Cytotechnology, vol. 16, pp. 1-15, 1994.

Sitaraman et al., "A novel cell-free protein synthesis system", Journal of Biotechnology, vol. 110, pp. 257-263, 2004.

Kim et al., "A highly efficient cell-free protein synthesis system from *Escherichia coli*", Eur. J. Biochem., vol. 239, pp. 881-886, 1996.

Kigawa et al., "Preparation of *Escherichia coli* cell extract for highly productive cell-free protein expression", Journal of Structural and Functional Genomics, vol. 5, pp. 63-68, 2004.

Ha et al., "Immunostimulation with *Escherichia coli* extract: prevention of recurrent urniary tract infections", International Journal of Antimicrobial Agents, vol. 31S, pp. S63-S67, 2008.

Hendrickson, W., "Determination of Macromolecular Structures from Anomalous Diffraction of Synchrotron Radiation", Science, vol. 254, No. 5028, pp. 51-58, 1991.

Spirin et al., "A Continuous Cell-Free Translation System Capable of Producing Polypeptides in High Yield", Science, vol. 242, No. 4882, pp. 1162-1164, 1988.

Kigawa et al., "Structure Determination of Protein Folds Using the Cell-free Synthesis and NMR Spectroscopy", Experimental Medicine, vol. 18, No. 18, pp. 60-64, 2000.

Ge et al., "Simultaneous Introduction of Multiple Mutations Using Overlap Extension PCR", Biotechniques, vol. 22, No. 1, pp. 28 and 30, 1997.

Kigawa et al., "Cell-free synthesis and amino acid-selective stable isotope labeling of proteins for NMR analysis", Journal of Bimolecular NMR, vol. 6, No. 2, pp. 129-134, 1995.

Ikura M., "Heteronuclear 3D NMR and isotopic labeling of calmodulin. Towards the complete assignment of the 1H NRM spectrum", Biochem. Pharmacol., vol. 40, No. 1, pp. 153-160, 1990.

Patzlaff et al., "An isotope-edited FT-IR study of a symporter, the lactose permease", Biochem., vol. 41, pp. 7366-7372, 2002.

Ikura et al., "A novel approach for sequential assignement of 1H, 13C, and 15N spectra of proteins: heteronuclear triple resonance three-dimensional NMR spectroscopy. Application to calmodulin.", Biochemistry, vol. 29, pp. 4659-4667, 1990.

Weber et al., "Inhibition of Protein Synthesis by Cl-", Journal of Biological Chemistry, vol. 252, No. 11, pp. 4007-4010, 1977.

Cooper et al., "Transcription of Vaccinia Virus mRNA Coupled to Translation in Vitro", Virology, vol. 88, No. 1, pp. 149-165, 1978.

Dougherty et al., "Translation of Potyvirus RNA in a Rabbit Reticulocyte Lysate: Reaction Conditions and Identification of Capsid Protein as One of the Products of in Vitro Translation of Tobacco Etch and Pepper Mottle Viral RNAs", Virology, vol. 101, No. 2, pp. 466-474, 1980.

Hardwick et al., "Cell-free protein synthesis by kidney from the aging female fischer F344 rat", Biochimica et Biophysica Acta, vol. 652, No. 1, pp. 204-217, 1981.

Mori et al., "Cell-free translation of carbamyl phosphate synthetase I and ornithine transcarbamylase messenger RNAs of rat liver. Effect of dietary protein and fasting of translatable mRNA levels", Journal of Biological Chemistry, vol. 256, No. 8, pp. 4127-4132, 1981.

Cosgrove et al., "Absence of age differences in protein synthesis by rat brain, measured with an initiating cell-free system", Neurobiology of Aging, vol. 8, No. 1, pp. 27-34, 1987.

Office Action mailed Aug. 10, 2010 in Japanese Application No. 2004-333250.

Bulleid et al., "Cell-free synthesis of enzymicatly active tissue-type plasminogen activator", Biochem. J., vol. 286 (Part 1), pp. 275-280, 1992.

Emmerich et al., "Characterisation of Protein Synthesis in Cell-Free Extracts from Different Mammalian Cells by their Sensitivity to Inhibitors of Polypeptide-Chain Initiation", Hoppe-Seyler's Z. Physiol. Chem., vol. 360, No. 8, pp. 1099-1111, 1979.

Evdokimova et al., "The major mRNA-associated protein YB-1 is a potent 5' cap-dependent mRNA stabilizer", The EMBO Journal, vol. 20, No. 19, pp. 5491-5502, 2001.

Svitkin et al., "Complete transition of the hepatitis C virus genome in vitro: membranes play a critical role in the maturation of all virus proteins except for NS3", Journal of Virology, vol. 79, No. 11, pp. 6868-6881, 2005.

Kodukula et al., "Biosynthesis of phosphatidylinositol-glycan (PI-G)-anchored membrane proteins in cell-free systems: PI-G is an obligatory cosubstrate for COOH-terminal processing of nascent proteins", Proc. Nati, Acad. Sci., vol. 89, No. 11, pp. 4982-4985, 1992.

Merola et al., "Folding of hepatitis C virus E1 glycoprotein in a cell-free system", Journal of Virology, vol. 75, No. 22, pp. 11205-11217, 2001.

Walter et al., Preparation of Microsomal Membranes for Cotranslation Protein Translocation, Methods in Enzymology, vol. 96, pp. 87-93, 1983.

Ishihara, G., et al., "Expression of G protein coupled receptors in a cell-free translational system using detergents and thioredoxin-fusion vectors," Protein Expression and Prufication, vol. 41, pp. 27-37 (2005).

Kalmbach, R., et al., "Functional Cell-free Synthesis of a Seven Helix Membrane Protein: in situ Insertion of Bacteriorhodopsin into Liposomes," J. Mol. Biol., vol. 371, pp. 639-648 (2007).

Office Action issued Jan. 19, 2012 in corresponding European Application No. 08846826.9.

* cited by examiner

METHOD OF USING CELL-FREE PROTEIN SYNTHESIS TO PRODUCE A MEMBRANE PROTEIN

TECHNICAL FIELD

Reference to Related Application

This application is based upon the priority of Japanese patent application No. 2007-286899, filed on Nov. 5, 2007, the disclosure of which is incorporated herein in its entirety by reference thereto.

The present invention relates to a method for producing a membrane protein using a cell-free protein synthesis system, and, particularly, to a method for efficiently producing a membrane protein synthesized by a cell-free protein synthesis system, the protein is in a state of being integrated into a lipid liposome.

BACKGROUND

Primary structures of proteins encoded by genome in various organisms have been revealed based on results of various genome projects. Approximately 30% of proteins in higher organisms have been presumed to be an endogenous membrane protein (integral membrane protein) having transmembrane helix. Membrane proteins are involved in signal transduction, mass transportation, energy production, formation of cytoskeleton etc. at cell membranes. In addition, the membrane protein is very important as a potential drug target. Actually, it is known that approximately 70% of commercially available pharmaceutical agents act on membrane proteins, especially on a G protein-coupled receptor. Protein 3000 Project in Japan which was conducted in consideration of the importance of protein structures has revealed stereostructures of more proteins than was initially expected and produced internationally great results. However, there are merely a few cases that have revealed the stereostructures of membrane proteins, since it is difficult to produce crystals of membrane proteins suitable for structural analysis.

The applicant of the present application has already developed a method for producing an insoluble protein using a cell-free protein synthesis system in the presence of detergent (surfactant) without the protein being insolubilized (see, for example, Patent Document 1 and Non-Patent Document 1). This method can be merely applied to a case where various membrane proteins can be abundantly synthesized as soluble fraction and a case where a detergent used does not inhibit protein synthesis. Accordingly, there are some detergents that cannot be selected for the method as those which contribute to the stabilization of the synthesized protein.

Moreover, a method for synthesizing a membrane protein having a biological function by merely adding a lipid liposome to a cell-free protein synthesis system is also reported (see Patent Document 2 and Non-Patent Document 2). However, it is considered that the method is not necessarily versatile, since the introducibility of membrane proteins into a liposome depends on their respective properties and the probability of contact between a synthesized polypeptide chain and a liposome is low.

[Patent Document 1] Japanese Patent Kokai Publication No. 2003-18999A
[Patent Document 2] Japanese Patent Kokai Publication No. 2005-225796A
[Non-Patent Document 1] Ishihara G. et al., (2005) Protein Expression and Purification, Vol. 41, pp. 27-37
[Non-Patent Document 2] Kalmbach, R. et al., (2007) Journal of Molecular Biology, Vol. 371, pp. 639-648

SUMMARY

The entire disclosures of Patent Documents 1 and 2 and Non-Patent Documents 1 and 2 as mentioned above are incorporated herein by reference thereto. An analysis of related art by the present invention is given below.

Although producing an active structure, the methods for producing membrane protein as disclosed in the above mentioned documents cannot provide sufficient yield and reproducibility according to an analysis as performed by the inventors of the present application. Thus, more efficient and universal methods are strongly desired.

The present invention is based on the finding that a functional form of a membrane protein can be synthesized abundantly by simultaneously progressing the protein synthesis using a dialysis method and the formation of a lipid bilayer membrane in a cell-free protein synthesis system in which a detergent (surfactant) and a lipid coexist. That is, the present invention provides a method for producing a membrane protein folded to its native or active structure in a lipid disk or liposome, comprising: (a) preparing a reaction solution for cell-free protein synthesis containing a polynucleotide encoding a membrane protein, a steroidal detergent and a phospholipid, wherein the steroidal detergent is contained at a concentration higher than its critical micelle concentration, (b) decreasing the concentration of the steroidal detergent in the reaction solution, and (c) synthesizing the membrane protein simultaneously with the formation of a lipid disk or liposome into which the synthesized membrane protein is integrated.

In a preferred mode, the membrane protein is synthesized by a cell-free protein synthesis reaction using a dialysis method, and the steroidal detergent is contained in the reaction solution at an initial concentration of 1.5 to 10 times, more preferably 2 to 5 times, higher than its critical micelle concentration. It is preferable that the steroidal detergent is digitonin, cholate or CHAPS. In one mode, in a case where a cell-free protein synthesis system [reaction] other than the dialysis method is used, it is preferable that (b) comprises adsorbing the detergent by using a resin capable of binding to the detergent. In another mode of the present invention the method further comprises: solubilizing the membrane protein from the (resultant) complex with the lipid disk or liposome to purify the membrane protein.

In another aspect, there is provided a composition comprising the membrane protein produced by the method of the present invention, which is in a state of being integrated into a lipid disk or liposome. The composition may be used for screening or delivery of a pharmaceutical agent.

According to the present invention, protein synthesis and liposome formation are performed around the same time, so that the synthesized polypeptide of high hydrophobicity is protected by a lipid disk during the liposome formation and aggregation of proteins is inhibited. In the early stage of the protein synthesis, for example in the case of using cholate, although the synthesis reaction is suppressed by the presence of a detergent (at a concentration) more than or equal to the critical micelle concentration, the synthesis is initiated when the concentration of the detergent is decreased. Furthermore, it is considered that folding formation of the protein as synthesized during fusion of the lipid disk is promoted and a membrane protein with a normal folding can be synthesized efficiently. Accordingly, the method of the present invention is universally usable for a variety of membrane proteins and useful as a method for mass production of a membrane protein.

PREFERRED MODES

"Membrane Protein"

Figure 1:
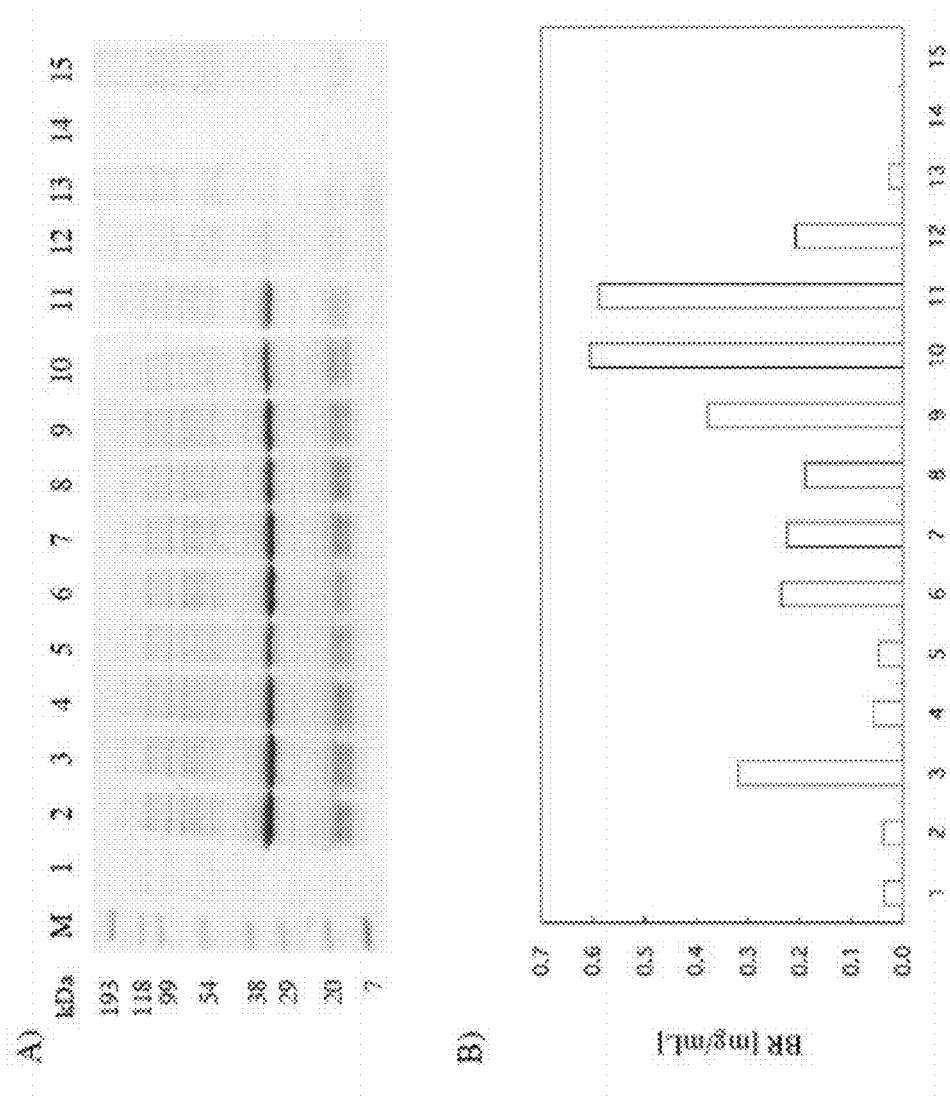
FIG. 1A and FIG. 1B show a result obtained from examination of the type of detergents for cell-free protein synthesis.

In the present application, the term "membrane protein" includes, in addition to an endogenous membrane protein (integral membrane protein) having a transmembrane helix (or helices), a protein whose portion as modified by palmitoylation, geranylation or myristoylation is embedded in membrane lipids, or a protein interacting with a membrane lipid(s) or membrane protein(s). For example, the membrane protein includes, but not restricted to, a receptor protein, a channel protein, a transporter (transporter protein), a membrane-bound enzyme and the like. Especially, an endogenous membrane protein having a transmembrane site(s) exhibits extremely poorly water-soluble property, since it has a hydrophobic amino acid sequence which is so arranged as to be readily integrated into membrane lipids. When these membrane proteins are expressed in heterologous hosts using a technique for DNA recombination, the membrane proteins are quickly aggregated to form their insoluble precipitations. Accordingly it is difficult to prepare a protein which has a biological activity and a correct stereostructure (tertiary structure). However, many of those membrane proteins have important functions such as intracellular signal transduction (signaling) and growth regulation, and thus are very important as a target for drug development (drug discovery).

The "signal transduction (signaling) pathway" is a medically important biological pathway which is regulated by a second messenger such as a G protein and cAMP. A protein involved in this signal transduction pathway includes, for example, a G protein-coupled receptor (GPCR) which binds to a ligand such as a peptide hormone and a neurotransmitter, a G protein itself, an effector protein such as phospholipase C, adenylate cyclase, phosphodiesterase and the like, as well as protein kinase A and protein kinase C.

A GPCR super family which is a membrane protein is also referred to as a seven-transmembrane receptor, since it has seven transmembrane sites for its α-helix. G protein to be coupled is usually a trimer made up of α, β and γ subunits. It is known that an extremely large number of ligands bind to the GPCR. Such ligand includes, for example, dopamine, adrenaline, endothelin, adenosine, muscarine, acetylcholine, serotonin, histamine, thrombin, kinin, a taste ingredient and an olfactory ingredient. Control of the activity of this receptor is effective in treating diseases relating to nerve, immune, blood pressure and metabolism. Although a large number of receptors are identified by a genome analysis of eukaryotic organisms and a comprehensive research tool is desired, conventional techniques have a problem that aggregation is readily caused in the case of large scale expression, since GPCR has extremely high hydrophobicity due to its structure having seven transmembrane regions.

Other cell membrane receptors include an ion channel receptor (ionotropic receptor) (such as glutamate receptor in brain), and the transporters include transporters from those for transporting a relatively low-molecular substance such as glucose or amino acid ranging to those for transporting a relatively large molecule such as a protein or DNA.

The membrane bound enzyme includes various proteins involved in intracellular signal transmission such as the above mentioned G protein, and plays an important role relating to cell growth regulation and cell carcinogenesis. In addition, the membrane bound enzyme includes not only these previously known membrane proteins, but novel membrane proteins whose existence is expected from their genomic information and whose functions however remain unclear. Furthermore, the membrane protein of the present invention includes even a partial sequence, a homologous sequence, a modified sequence and an inducible sequence of those proteins, which, basically, interact with a lipid bilayer membrane.

Polynucleotides encoding those membrane proteins are a nucleic acid polymer of any length made up of either of ribonucleotides or deoxyribonucleotides. In addition, they are DNA or RNA of single-strand or double-strand. Moreover, they may be subjected to previously known modification, and may be labeled with a fluorescent substance, methylated, imparted with a cap structure, or substituted with a nucleotide analogue.

In the case of a DNA, the polynucleotide is usually double strand and may be cyclic double-strand or linear double-strand, which may be used for transcription and translation in a cell-free protein synthesis system. They can be produced by conventional techniques for DNA recombination which are well known to a person skilled in the art, and in which E. coli and the like are used as a host. Alternatively, they can be prepared by techniques for in vitro DNA amplification, such as PCR, without transforming a host cell. In the case of RNA, they are usually used as a single-strand mRNA, and translated in a cell-free protein synthesis system. These techniques are disclosed in, for example, Sambrook et al., Molecular Cloning: A Laboratory Manual, Second Edition, 1989 <Reference 1>; D. N Glover (ed.), DNA Cloning, Volumes I and II, 1985; M. J. Gait (ed.), Oligonucleotide Synthesis, 1984 <Reference 2> etc.

As a sequence required for transcription or translation in a cell-free protein synthesis system, for example, a sequence such as a potent promoter such as a T7 promoter, a ribosome binding site and a T7 terminator may be added, and also a tag sequence, such as histidine or GST, for efficiently purifying an expressed fusion protein may be added.

[Cell-Free Protein Synthesis System]

A cell-free protein synthesis system used in a method of the present invention is a system in which a protein is in vitro synthesized using a cell extract solution. Such system may be a cell-free translation system in which the information of mRNA is read and a protein is synthesized on a ribosome, or a system comprising both of a cell-free transcription system in which RNA is synthesized using DNA as a template and the cell-free translation system. In the case of using DNA as a template, simultaneous parallel preparation of numerous template DNAs may be done rapidly by an in vitro amplification reaction, such as PCR, without performing a complicated manipulation as cloning which was required previously.

As the above mentioned cell extract solution, an extract solution is usable which is obtained from a eukaryotic or prokaryotic cell containing components (or ingredients) required for protein synthesis such as a ribosome and tRNA. As the above mentioned eukaryotic cell and prokaryotic cell, any previously known cells are usable. Such cells include, as a concrete example, *E. coli*, thermophilic bacteria, wheat germ, rabbit reticulocyte, mouse L cell, Ehrlich's ascitic cancer cell, HeLa cell, CHO cell and budding yeast and the like. Especially, cell extract solution derived from *E. coli* (for example, *E. coli* S30 cell extract solution) or from *Thermus thermophilus* is desirable due to their abilities to achieve high synthetic yield. The *E. coli* S30 cell extract solution can be prepared from *E. coli* A19 (rna, met), BL21, BL21 star, BL21 codon plus strain and the like according to known methods (see, Pratt, J. M. et al., Transcription and translation—a practical approach, (1984), pp. 179-209, Henes, B. D. and Higgins, S. J. ed., IRL Press, Oxford <Reference 3>), or is commercially available from Promega or Novagen, which may be used.

A concrete method for preparation of *E. coli* S30 cell extract solution is as follows: First, *E. coli* cells are cultured and harvested by centrifugation and the like. The harvested bacterial cells are washed, and then resuspended in a buffer solution and destructed using French press, glass beads, Waring blender and the like. Insoluble substances of the destructed *E. coli* cells are removed by centrifugation, and the remaining is mixed with a pre-incubation mixture to be incubated. Endogenous DNA and RNA are degraded by this manipulation. In addition, however, it may be done to degrade endogenous nucleic acids by supplementation of a calcium salt, a nuclease from *Micrococcus* and the like. Subsequently, endogenous amino acid, nucleic acid, nucleoside etc. are removed by dialysis and the resulting solution is aliquoted to preserve in liquid nitrogen or at −80° C.

A reaction solution for cell-free protein synthesis of the present invention contains, in addition to a crude cell extract solution from *E. coli* S30 and the like, a polynucleotide (such as mRNA) encoding a membrane protein, a steroidal detergent and a phospholipid. In addition, the reaction solution may contain ATP (0.5 to 5 mM), GTP (0.005 to 1.0 mM), CTP (0.005 to 1.0 mM), UTP (0.005 to 1.0 mM), buffer, salts, amino acids, RNase inhibitors, antibacterial agents, and, as necessary, an RNA polymerase (in the case of using a DNA as a template), tRNA and the like. Also, an ATP regenerating system, polyethylene glycol (for example, PEG#8000), 3',5'-cAMP, folic acids (0.1 to 5 mM), reducing agents (for example, 1 to 10 mM dithiothreitol) may be contained.

As the buffer, a buffer agent such as Hepes-KOH, Tris-OAc and the like may be used. As the salts, acetates (for example, ammonium salt, magnesium salt etc.), glutamate and the like may be used. As the antibacterial agent, sodium azide, ampicillin and the like may be used. In the case of using DNA as a template, an RNA polymerase is added to the reaction system, wherein a commercially available enzyme such as a T7RNA polymerase may be used.

In the present invention, the ATP regenerating system includes, but not restricted to, a combination of preferably 0.02 to 5 μg/μl creatine kinase (CK) and preferably 10 to 100 mM creatine phosphate (CP). For such system, any previously known substances are also usable. As materials other than those as mentioned above, for example, a combination of 1 to 20 mM phosphoenol pyruvate (PEP) and 0.01 to 1 μg/μl pyruvate kinase (PK) and the like are usable. Both of PK and CK are enzymes which regenerate ATP from ADP, and require PEP and CP, respectively, as substrates.

To the cell-free protein synthesis system of the present invention there may be applied, in addition to a batch method and a flow method, any previously known techniques (see, for example, Spirin, A et al., Methods in Enzymol., 217, 123-142, 1993 <Reference 4>) Among them, in order to simultaneously perform synthesis of a membrane protein and decrease of the concentration of the detergent in a reaction solution, a dialysis method is preferable in which internal solution and external solution are separated via a dialysis membrane (ultrafilter) during shaking or stirring. As equipment for dialysis, for example, DispoDialyzer (registered trademark) (Spectrum), Slidealyzer (registered trademark) (Pierce) or Spectra/Por (registered trademark) dialysis tube (Spectrum) may be used. The detail of a cell-free protein synthesis system using a dialysis method which has been improved by the applicant is disclosed in Japanese Patent Kokai Publication No. 2000-175695A <Reference 5>, the disclosure of which is incorporated herein in its entirety by reference thereto. Here, it is to be noted that the disclosures of the above mentioned References 1-4 are incorporated herein in their entirety by reference thereto.

[Detergent]

The detergent (or surfactant) which is used for a method of the present invention is a steroidal detergent which is excellent in affinity for a hydrophobic region of a protein and for lipid without depending on the type of a membrane protein. The steroidal detergent usable for the method of the present invention include, but not restricted to, cholate, taurocholate, glycocholate, deoxycholate, taurodeoxycholate, glycodeoxycholate, digitonin, 3-[(3-cholamidepropyl) dimethylammonio]-1-propanesulfonate (CHAPS), 3-[(3-cholamidopropyl)dimethylammonio]-2-hydroxy-1-propanesulfonate (CHAPSO). These detergents may be a relatively mild one which suppresses aggregation of proteins and stabilizes them by interaction therewith, and may also be a detergent which inhibits cell-free protein synthesis reaction at an initial concentration. The reason is that the protein synthesis reaction is started along with decrease of the concentration of the detergent and the synthesized proteins are integrated into lipid disk(s) as the growth of the lipid disk(s) proceeds. A concentration as usually used may be around 1 to 10 times higher than the critical micelle concentration (cmc) of the detergent, and the concentration may be an initial concentration which is at least higher than cmc. This cmc value represents a concentration at which the detergent forms an amphiphilic micellar structure in water, and the excess of this concentration results in generation of a micelle. That is, the cmc value, basically, reflects the solubility of a detergent in water. In the case of (a concentration) higher than the cmc value, a concentration of dissolved monomer of detergent is constant.

In the case of decreasing the detergent concentration using a dialysis method, the initial concentration of the steroidal detergent is preferably approximately 1.5 to 10 times, more preferably approximately 2 to 5 times higher than cmc. In the case of the concentration being lower than 1.5 times as high as cmc, the concentration of the detergent is decreased at the same time with starting of dialysis so that sufficient time for integration of the synthesized membrane protein into a lipid disk cannot be secured, since growth speed of the lipid disk is too fast. On the other hand, it is considered that in the case of the concentration being higher than 10 times as high as cmc, long time is required for decrease of the concentration of the detergent by dialysis, as a result of which folding of the synthesized membrane protein is not sufficient due to decrease of the growth speed of a lipid disk In this mode, it is possible to optimize synthetic yield of a functional form of a membrane protein by suitably adjusting the type and concentration of the detergent used as mentioned above.

[Phospholipid]

The phospholipid usable for a method of the present invention includes phosphatidylcholine (PC), phosphatidylethanolamine (PE), phosphatidylserine (PS), phosphatidylinositol (PI), phosphatidylglycerol (PG), phosphatidic acid, cardiolipin, sphingomyelin, egg-yolk lecithin, soybean lecithin, hydrogenated form thereof etc. The phospholipid may contain also glycoglycerolipid or glycosphingolipid, and also the phospholipid in combination with one or more kinds of those glycolipids may be used.

[Synthesis of Proteoliposome]

Figure 5:
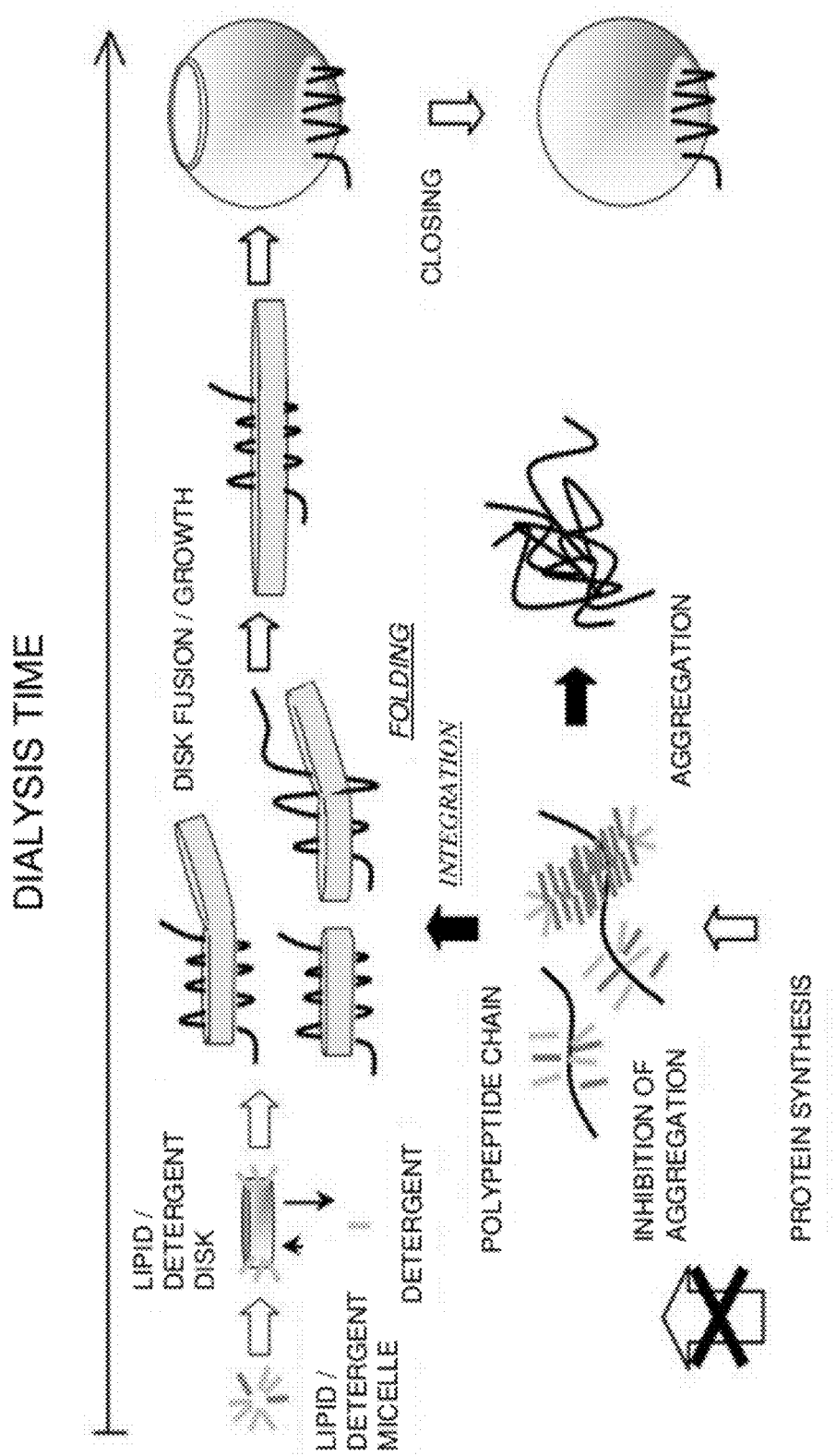
FIG. 5 shows a schematic figure representing a model of a process of functional expression in a cell free system by the present invention.

The present invention provides a method for producing a membrane protein (proteoliposome) which is folded to its native or active structure in a lipid disk or liposome. FIG. 5 schematically shows a process of a cell-free protein synthesis reaction using a dialysis method as a typical method of the present invention. First, (a) a reaction solution for a cell-free protein synthesis containing a polynucleotide encoding a membrane protein, a steroidal detergent, and a phospholipid is prepared. Here, it is required that the steroidal detergent is present at a concentration higher than its critical micelle concentration (cmc). Immediately after start of protein synthesis reaction, the concentration of the detergent is high, so that the phospholipid is associated with the detergent to form a small disk. In this stage, the protein synthesis reaction may be inhibited by the detergent. For example, sodium cholate which is a preferable detergent is an anionic detergent comprising a steroidal hydrophobic group. Although inhibiting protein synthesis at a concentration higher than or equal to cmc, the sodium cholate is suitable to be removed by dialysis. The membrane protein synthesized as the concentration of the detergent decreases aggregates if left as-is, but is integrated into a lipid bilayer membrane with inhibiting the aggregation if associated with a lipid disk. When the concentration of the detergent is further decreased, the lipid membrane grows while folding of the integrated membrane protein proceeds. It is considered that the lipid disk grows, via the formation of a spherical open type-liposome, finally to a closed type-liposome. In a case where the detergent forms a large micelle, the micelle may be dispersed into monomers before dialysis by diluting the reaction solution, or may be dispersed by mixing with cholate salt etc.

In a case where a method other than the dialysis method is used to a cell-free protein synthesis system, a detergent can be removed by using a general property of the detergent such as hydrophobicity or electric charge. For example, a method for hydrophobic adsorption makes use of a property of the detergent that binds to hydrophobic resin. Generally, a predetermined amount of resin is added to a solution containing a detergent and the mixture is left still at 4° C. or room temperature. The resin to which the detergent binds can be removed by centrifugation or filtration. Furthermore, in a case where an amphiphilic detergent is used, a condition that allows the micelle containing a membrane protein to be adsorbed on an ion exchange resin and the micelle containing no membrane protein to pass through can be selected.

[Analysis of Structure and Function of a Membrane Protein, as Well as Application Thereof to a Pharmaceutical Composition]

A membrane protein as produced by a method of the present invention has an activity in a state as integrated into a lipid disk or liposome. Accordingly, the method of the present invention is useful for large scale preparation of the membrane protein as stabilized to its native or active structure. The synthesized membrane protein may be used as-is for a study of functional analysis and a study of structural analysis. The study of structural analysis can be used to determine an activity of the membrane protein by detecting mass transportation via a lipid bilayer membrane, and a bond with a ligand. The technique for functional analysis can be used for high-throughput screening which employs enzyme activity of a receptor protein or its connectivity to a ligand as an indicator. For example, a substance acting on a receptor protein is identified by using a peptide, a protein or a combinatorial library of compounds. In order to demonstrate a bond of a specific ligand which binds to GPCR or identify an inhibitor and competitor thereof, various ligand molecules can be labeled with radioisotope, fluorescent substance, luminescent compound and the like to analyze a bond with a receptor protein.

The study of structural analysis may be carried out by, but not restricted to, X-ray crystallography analysis, nuclear magnetic resonance (NMR) analysis, small-angle X-ray scattering (SAXS), scanning probe microscopy (SPM), atomic force microscopy (AFT) and the like. Crystallization for X-ray diffraction can be made by using a protein which remains integrated in a liposome, or also by solubilizing and purifying the membrane protein from a liposome. Various methods have been also reported for crystallizing a receptor protein in a state in which the protein is present in phospholipid bilayer membrane (see JP Patent Kokai Publication No. 2006-219401<Reference 6>), the disclosure of which is incorporated herein in its entirety by reference thereto.

A proteoliposome as produced by a method of the present invention can be further used as a pharmaceutical composition by integrating a low-molecular pharmaceutical agent thereinto. A membrane protein such as drug transporter and multidrug efflux pomp is used by being integrated into a liposome together with a low-molecular pharmaceutical agent which can be transported thereby. Administered to a living body, a pharmaceutical composition containing those, during circulation in the body, can deliver a drug of interest depending on an environment where various types of organs exist. By regulating, for example, pH and temperature condition in the living body, the composition uses them as indication to release the pharmaceutical agent.

In one mode of the present invention, integration of a hydrophobic therapeutic agent into a hydrophobic core which constitutes the above mentioned pharmaceutical composition can elongate the circulatory lifetime of the agent and provide an effect of sustainedly releasing the agent. Such hydrophobic agent includes, but not restricted to, for example, a photodynamic therapeutic agent such as psoralen and porphyrin, an anticancer agent such as tamoxifen, paclitaxel, adriamycin, daunorubicin etc., cholesterol-lowering agent and an antibacterial agent such as vancomycin etc.

In addition, in another mode of the present invention, a viral protein or a tumor antigen may be expressed as a membrane protein, and an immunogenic composition containing it may be used as a component of vaccine. The viral protein includes gp120 of human immunodeficiency virus, envelope glycoprotein of herpes simplex virus, spike protein of SARS virus, and hemagglutinin of influenza virus, and the like. An antigen which aids immune response includes a pathogen such as bacteria, and a membrane protein on the surface of a tumor cell.

The present invention will be explained in further detail by the examples as mentioned below, but the scope of the present invention is not restricted to the examples.

EXAMPLES

Example 1

Functional Expression of Bacteriorhodopsin (BR) Derived from Extreme Halophile *Halobacterium salinarum* in Cell Free System BR is a light-driven proton pump which is a seven-transmembrane α-helical membrane protein. BR has all-trans retinal as a chromophore, covalently binds to a lysine residue at position 216, and exhibits maximum absorbance at the wavelength of around 570 nm. When absorbing the light of around 570 nm, the all-trans retinal is photoisomerized to 13-cis-retinal. Along with the photoisomerization, the conformation of BR is changed and a reaction occurs which BR is returned to its initial state via its various photochemical reaction intermediates temperature-dependently. During the serial process, a proton is transported from the cytoplasmic side to the extracellular side.

1) Preparation of a BR Synthetic Plasmid

A synthetic plasmid was prepared by amplifying a fragment comprising a native His tag having a recognition site of TEV (Tobacco Etch Virus) (MKDHLIHNVHKEEHA-HAHNKDYDIPTTENLYFQGSSG SSG: SEQ ID NO.:1), T7 promoter and T7 terminator by using 2-step PCR, and incorporating the fragment into a pCR2.1 vector. An *E. coli* expression vector for BR as used as a template (Shimono, K. et al., J. Biol. Chem., (2003) 278, 23882-23889 <Reference 7>) was supplied from Dr. KAMO Naoki in Hokkaido Univ. PCR was performed using 5'-primer; 5'-tccagcggctcctcggga-caggcccagatcacc-3' (SEQ ID NO.:2) and 3'-primer; 5'-gggcggggatcaatcaatcattatcagtcgctggtcgcg-3' (SEQ ID NO.:3) to amplify a gene encoding BR from the amino acid residue thereof at position 14. Subsequently, with the first PCR product used as a template, second PCR was performed using two chemical synthetic double stranded DNA fragments (5' fragment encoding T7 promoter sequence, N-terminal native His tag, and TEV protease recognition site, and 3' fragment encoding T7 terminator sequence) which partially overlapped with the first PCR product at both terminus regions, and using 5',3'-primer; 5'-gctcttgtcattgtgcttcg-3' (SEQ ID NO.: 4). As a result, a fragment was obtained into which an N-terminal native His tag, and a sequence encoding a TEV protease recognition site, a linker sequence and a BR fusion protein with partial deletion at the N terminus were inserted between a 5' upstream T7 promoter sequence and a 3' downstream T7 terminator sequence. This fragment was subjected to TA-cloning into pCR2.1-TOPO (Invitrogen) to obtain a BR synthetic plasmid. Here it is to be noted that the disclosure of the Reference 7 as mentioned above is incorporated herein in its entirety by reference thereto.

2) Synthesis of BR by a Method for Cell-Free Protein Synthesis

A protein synthesis reaction was performed as follows: an internal solution of the composition as shown in table 1 as mentioned below was supplied with 100 µM all-trans retinal at final concentration (Sigma), 9 µg of synthetic plasmid as necessary, a predetermined concentration of a detergent, and 6 mg of egg yolk phosphatidylcholine (Type XVI-E, Sigma) to prepare a reaction solution, 0.9 ml of which was poured into a dialysis membrane (Spectra/Por 7, Molecular Weight Cut Off: 15000, Spectrum). The synthesis reaction was performed at 30° C. for 6 h during dialysis which was to 10 times volume of external solution (9 mL) in a 15 mL conical tube by rotary shaking with a rotary shaker (RT-50, TAITEC). In the case of a detergent and lipid being added, the detergent having a concentration of 10 times higher than the predetermined concentration and an aqueous solution of the lipid were mixed in advance, and the resulting solution was agitated for 1 h at room temperature to be added to the reaction internal solution.

TABLE 1

| Reaction solution (internal solution of dialysis) | 900 µL | External solution of dialysis | 9 mL |
|---|---|---|---|
| 1.6M Mg(OAc)$_2$ | 5.7 µL | 1.6M Mg(OAc)$_2$ | 0.06 mL |
| LMCPY-tRNA | 336 µL | LMCPY-tRNA | 3.36 mL |
| 0.75 g/L Tyrosine | | | |
| 160 mM HEPES-KOH (pH7.5) | | | |
| 10.70% PEG8000 | | | |
| 534 mM K-Glu | | | |
| 5 mM DTT | | | |
| 1.07 mM ATP | | | |
| 2.40 mM ATP, GTP, CTP, UTP | | | |
| 96 mg/L folic acid | | | |
| 1.78 mM cAMP | | | |
| 74 mM ammonium acetate | | | |
| 214 mM creatine phosphate | | | |
| 20 mM 20 Amino acids-Y | 67.5 µL | 20 mM 20 Amino acids-Y | 0.68 mL |
| 3.75 mg/mL creatine kinase | 60 µL | | |
| 17.5 mg/mL tRNA | 9 µL | | |
| S30 extract (OD260, approximately 200) | 270 µL | S30 buffer | |
| 60 mM KOAc | | 60 mM KOAc | |
| 10 mM Tris-OAc PH 8.2 | | 10 mM Tris-OAc PH 8.2 | |

TABLE 1-continued

| Reaction solution (internal solution of dialysis) | 900 μL | External solution of dialysis | 9 mL |
|---|---|---|---|
| 16 mM Mg(OAc)$_2$ 8.94 mM DTT 10 mg/mL T7 RNA polymerase 5% NaN$_3$ | 6 μL 9 μL | 16 mM Mg(OAc)$_2$ 8.94 mM DTT 5% NaN$_3$ | 0.09 mL |

3) Estimation of the Amount of an Active BR by Determination of Visible Absorbance After termination of the synthesis reaction, the reaction internal solution was centrifuged at 15000 rpm for 10 min. (MX-301, TOMY) to separate into supernatant and precipitate. The precipitate was suspended in 900 μL of 50 mM Tris-HCl (pH 7.0), 400 mM NaCl. The precipitate suspension of 20 μL or 50 μL was supplied with 10 μL of 10% (w/v) dodecyl-D-maltoside (DDM, Anatrace) to adjust to 50 mM Tris-HCl (pH 7.0), 400 mM NaCl, and 1% (w/v) DDM at final concentration, and was, immediately after vortexing, centrifuged at 15000 rpm for 10 min. (MX-301, TOMY) to separate into supernatant and precipitate. The centrifuged supernatant was recovered to immediately determine visible absorption spectrum of wavelengths from 250 nm to 750 nm by a spectrophotometer (U-2810, Hitachi). Scatter correction was performed by subjecting the determined scores from 680 nm to 750 nm to linear regression to subtract from the measured spectrums. The amount of an active BR was calculated from the score of the spectrum of 560 nm as subjected to the scatter correction using the molar absorption coefficient: 42000 and the molecular weight: 31.4 k.

4) Examination of Effects of Detergents in Cell Free Synthesis of BR

FIG. 1 shows a result of examination on whether a functional BR can be synthesized by adding various kinds of detergents and egg yolk phosphatidylcholine to a cell-free protein synthesis system using a dialysis method. FIG. 1(A) shows a result obtained by centrifuging the synthetic reaction solution, and subjecting 1 μL of the resulting precipitate to SDS-PAGE (XV PANTERA Gel 10-20%) and to CBB staining. FIG. 1(B) shows the amount of an active form as estimated from visible absorbance of the synthesized precipitate according to the above mentioned method. Lane 1 shows a control in which DNA and detergent/PC were not added, and Lane 2 shows a control in which detergent/PC was not added. Detergents as added to Lanes 3-15 were as follows: Lane 3: SUV; Lane 4: MLV; Lane 5: 1% OG/PC; Lane 6: 0.03% Triton X 100/PC; Lane 7: 0.02% DDM/PC; Lane 8: 0.02% Brij58/PC; Lane 9: 0.2% digitonin/PC; Lane 10:1% sodium cholate/PC; Lane 11: 1% CHAPS/PC; Lane 12: 0.5% deoxysodium cholate/PC; Lane 13: 2% pentadecafluorooctate (PFO)/PC; Lane 14: 1% lauryl sarcosine/PC; Lane 15: 0.5% SDS/PC. The concentrations of the detergents are all represented by concentration of weight per volume % (w/v %). MLV (multi lamellar vesicle) was prepared by dissolving egg yolk phosphatidylcholine (TypeXVI-E, Sigma) in chloroform so as to be 100 mg/mL, and subjecting the solution to vacuum drying with rotary evaporator to produce a thin membrane, followed by suspending it with vigorous vortex in sterilized distilled water so as to be 100 mg/mL. SUV (small unilamellar vesicle) was prepared by subjecting MLV to sonication of 90 W, for 30 sec.×3 times (VP-30s, TAITEC) on ice.

In comparison of the other conditions, BR was efficiently synthesized which kept its structure as it was synthesized under the co-existence of a steroidal detergent (digitonin (Lane 9), sodium cholate (Lane 10), CHAPS (Lane 11)) and egg yolk phosphatidylcholine (FIG. 1(B)).

Figure 2:
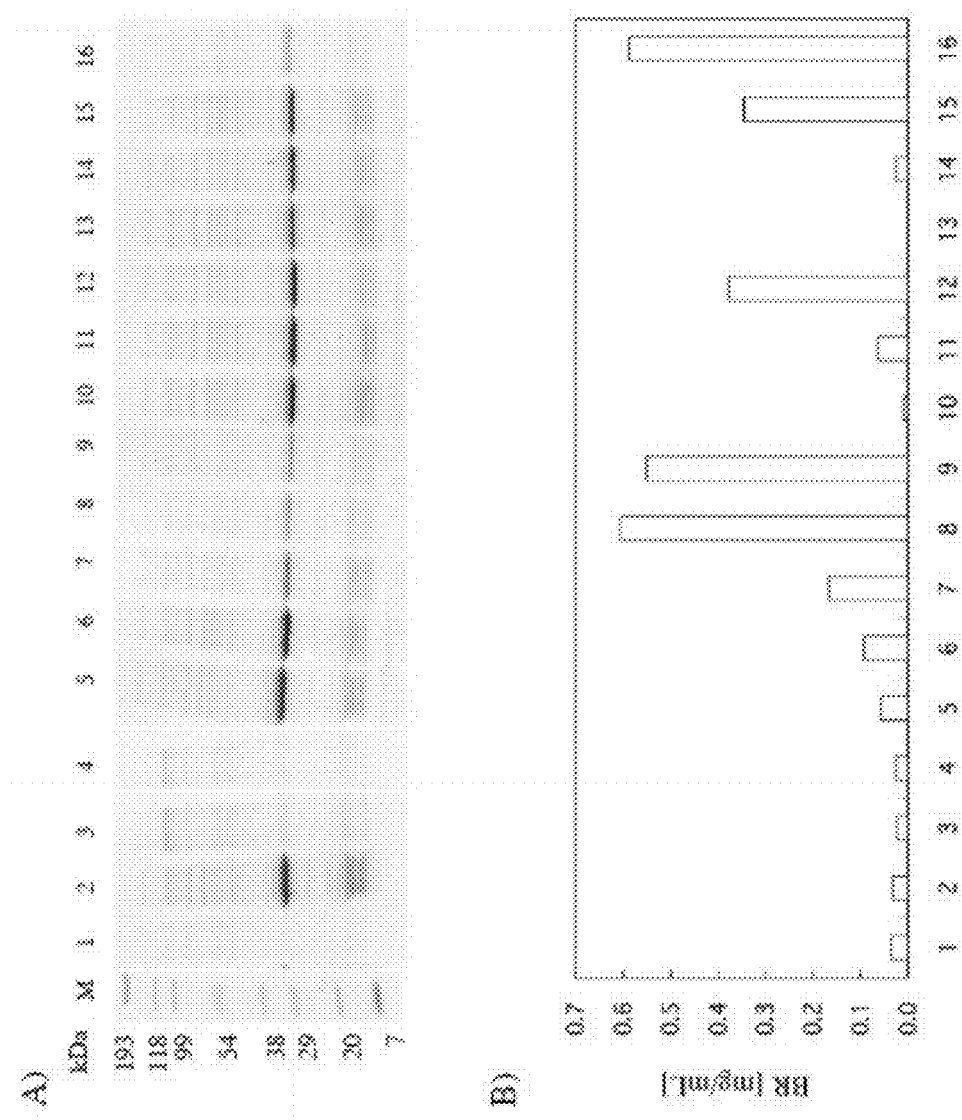
FIG. 2A and FIG. 2B show examination of concentrations of the detergents for cell-free protein synthesis.

In addition, FIG. 2 shows a result of addition of sodium cholate under various conditions, and a result of concentration dependency of digitonin and CHAPS. FIG. 2(A) shows a result obtained by adding various kinds of detergents and egg yolk phosphatidylcholine to a cell-free protein synthesis system using a dialysis method to centrifuge the synthetic reaction solution, and subjecting 1 μL of the resulting precipitate to SDS-PAGE (XV PANTERA Gel 10-20%) and CBB staining. As a molecular weight marker (Lane M), 1 μL of Prestained SDS-PAGE Standards Broad Range (Bio-Rad) was subjected to electrophoresis. Detection was performed by CBB staining. FIG. 2(B) shows the amount of an active form as estimated from visible absorbance of the synthesized precipitate. Lane 1:1% sodium cholate/PC without DNA; Lanes 2-15: addition of DNA; Lane 2: 1% sodium cholate/PC; Lane 3: 1% sodium cholate/PC (internal and external solution); Lane 4: 1% sodium cholate/PC (internal solution) and 1% sodium cholate (external solution); Lane 5: MLV; Lane 6: 0.2% sodium cholate/PC; Lane 7: 0.5% sodium cholate/PC; Lane 8: 1% sodium cholate/PC; Lane 9: 2% sodium cholate/PC; Lane 10: 0.03% digitonin/PC; Lane 11: 0.06% digitonin/PC; Lane 12: 0.2% digitonin/PC; Lane 13: 0.1% CHPAS/PC; Lane 14: 0.3% CHPAS/PC; Lane 15: 0.5% CHPAS/PC; Lane 16: 1% CHPAS/PC. The concentrations of the detergents are represented by concentration of weight per volume % (w/v %). Furthermore, although not shown in FIG. 2, it has been found that an active form can be recovered at the same or more amount as Lane 12 in FIG. 2 under the condition of 0.4% digitonin/PC.

From the results of FIG. 2, it is evident that the rate of the active form increases in a concentration-dependent manner. Significant increase was found in the case of a concentration being more than or equal to the critical micelle concentration (cmc) (Lane 8 (1% (w/v) sodium cholate), Lane 12 (0.2% (w/v) digitonin, and Lane 15 (0.5% (w/v) CHAPS)). Each detergent's cmc is as follows: sodium cholate: 0.41% (w/v), digitonin: 0.06% (w/v), and CHAPS: 0.49% (w/v). In the case of synthesis being performed while keeping the cholate concentration by addition of sodium cholate to internal and external dialysis solutions, synthesis of BR was not found (FIG. 2, Lanes 3, 4). Therefore, it is considered that cholate has an effect of inhibiting protein synthesis.

5) Confirmation of Integration to a Lipid Bilayer Membrane by Sucrose Density Gradient Centrifugation BR was synthesized using the same manner as the above mentioned method under the co-existence of 1% (w/v) sodium cholate/egg yolk phosphatidylcholine, and after termination of the synthesis reaction the reaction internal solution was centrifuged at 15000 rpm for 10 min (MX-301, TOMY) to separate into supernatant and precipitate. The precipitate was suspended in 900 μL of PBS, 10 mM EDTA, and ultracentrifuged at 100000×g for 30 min. (CS120GX, Hitachi), and then the resulting precipitate was washed. In addition, the precipitate was suspended in 900 μL of 50 mM Tris-HCl (pH 7.0), 400 mM of NaCl, and ultracentrifuged at 100000×g for 30 min. (CS120GX, Hitachi), and then the resulting precipitate was washed. This manipulation was repeated twice. The washed precipitate was suspended in 900 µL of 50 mM Tris-HCl (pH 7.0), 400 mM NaCl, and subjected to sonication on ice at 90 W for 30 sec.×3 times (VP-30s, TAITEC). Then centrifugation was performed at 5000 rpm for 5 min. (MX-301, TOMY) to separate into supernatant and precipitate. The centrifuged supernatant was adjusted to 1 mL with 50 mM Tris-HCl (pH 7.0), 400 mM NaCl, and piled up on 10 (2.5 mL), 30 (2 mL), 40 (2 mL), 50 (2.5 mL) % (w/v) solutions for sucrose density gradient as prepared in advance, and then ultracentrifuged with SW41Ti rotor at 100000×g for 10 h (L-80XP, Beckman), followed by fractionation being performed by 1 mL from the upper side.

Each fraction was subjected to confirmation of the presence of protein by SDS-PAGE, estimation of the amount of an active form by visible absorbance measurement, and quantitative determination of phospholipid by colorimetric method with phosphomolybdic acid. SDS-PAGE was performed according to a standard method, and detection was conducted with Coomassie Brilliant Blue (CBB) staining. The visible absorbance measurement was performed in the same manner as the above mentioned method. The method for quantitative determination of phospholipid by a colorimetric method with phosphomolybdic acid is as follows: 100 µL of the fraction as obtained from the density gradient centrifugation was collected, to which 100 µL of methanol and 100 µL of chloroform were added to be subjected to vigorous vortex, followed by the mixture being centrifuged at 15,000 rpm for 1 min. (MX-301, TOMY) to separate into two layers. The chloroform layer was fractionated, and, after removing chloroform by vacuum dryer (MV-100, TOMY), suspended in 100 µL of ultrapure water. The resulting suspension was transferred to a glass test tube, in which 250 µL of 10N sulfuric acid was then added, and the mixture as obtained was heated on heat block (DTU-1C, TAITEC) at 170° C. for 2 h. The mixture was supplied with 20 µL of 30% hydrogen peroxide, and further heated at 170° C. for 1 h. After cooling, 100 µL of 5% phosphomolybdic acid solution, 2.2 mL of ultrapure water, and 100 µL of Fisk-Sabbarow reagent (7.5 g of sodium bisulfite, 0.25 g of sodium sulfite and 0.125 g of 1-amino-2-naphthol-4-sulfonate/50 mL) was added to the mixture, which was then subjected to vortex to be heated at 100° C. for 5 min. After cooling, absorbance at 750 nm was measured on a plate reader (Model-680, BioRad). In order to make a calibration curve, 10, 20, 30, 40, and 50 µL of 2 mM sodium dihydrogenphosphate solution were measured in the same manner to perform quantitative determination of the samples.

Figure 3:
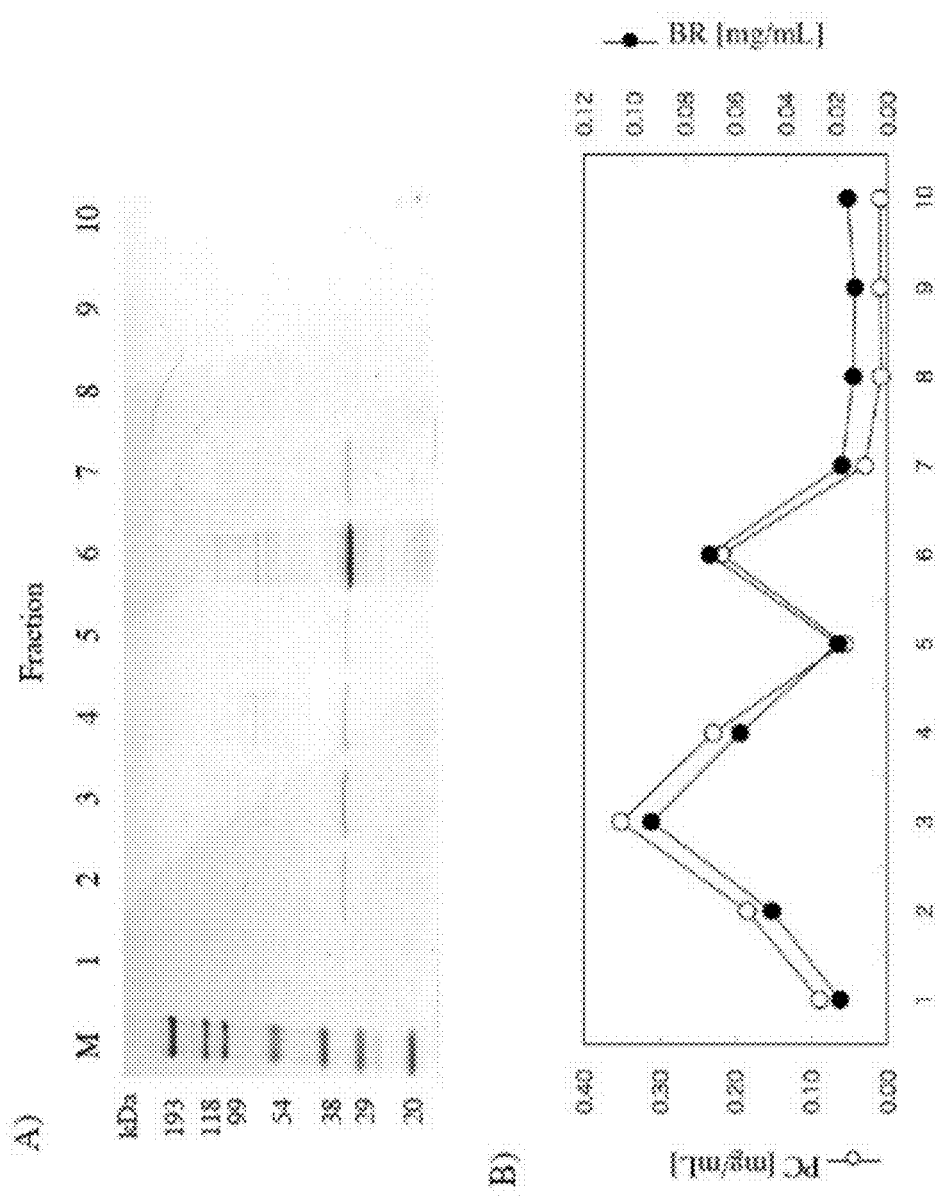
FIG. 3A and FIG. 3B show separation of a cell free synthesized BR from a liposome by density gradient centrifugation.

FIG. 3 shows a result of the foregoing. FIG. 3(A) shows a result obtained by subjecting each fraction of 2 µL to SDS-PAGE and CBB staining, and FIG. 3(B) shows the amount of an active form as estimated from visible absorbance of each fraction (●) and the amount of phospholipid by colorimetric method with phosphomolybdic acid (○). It was able to be confirmed that the synthesized BR was integrated in a phospholipid liposome, since the protein fractions (FIG. 3(A), Lanes 3, 6) and the phospholipid fraction (FIG. 3(B), ○ hollow circle) were present in the same fraction. In addition, the BR in which the normal folding is kept is mainly present in Fractions 3, 6 (FIG. 3(B), ● solid circle), and the profile of the amount of BR is identical to that of phospholipid. Accordingly, it was confirmed that the membrane protein BR with its normal structure retained was able to be synthesized in a phospholipid liposome.

6) Analysis of the Process of Functional Synthesis

BR was synthesized using the same manner as the above mentioned method under the co-existence of 1% (w/v) or 2% (w/v) sodium cholate/egg yolk phosphatidylcholine, and the reaction internal solution was diluted with sterilized ultrapure water to twice volume at arbitrary timing to terminate the reaction. The diluted reaction solution was centrifuged at 15000 rpm for 10 min. (MX-301, TOMY) to separate into supernatant and precipitate. The precipitate was suspended in 50 mM Tris-HCl (pH 7.0), 400 mM NaCl.

Figure 4:
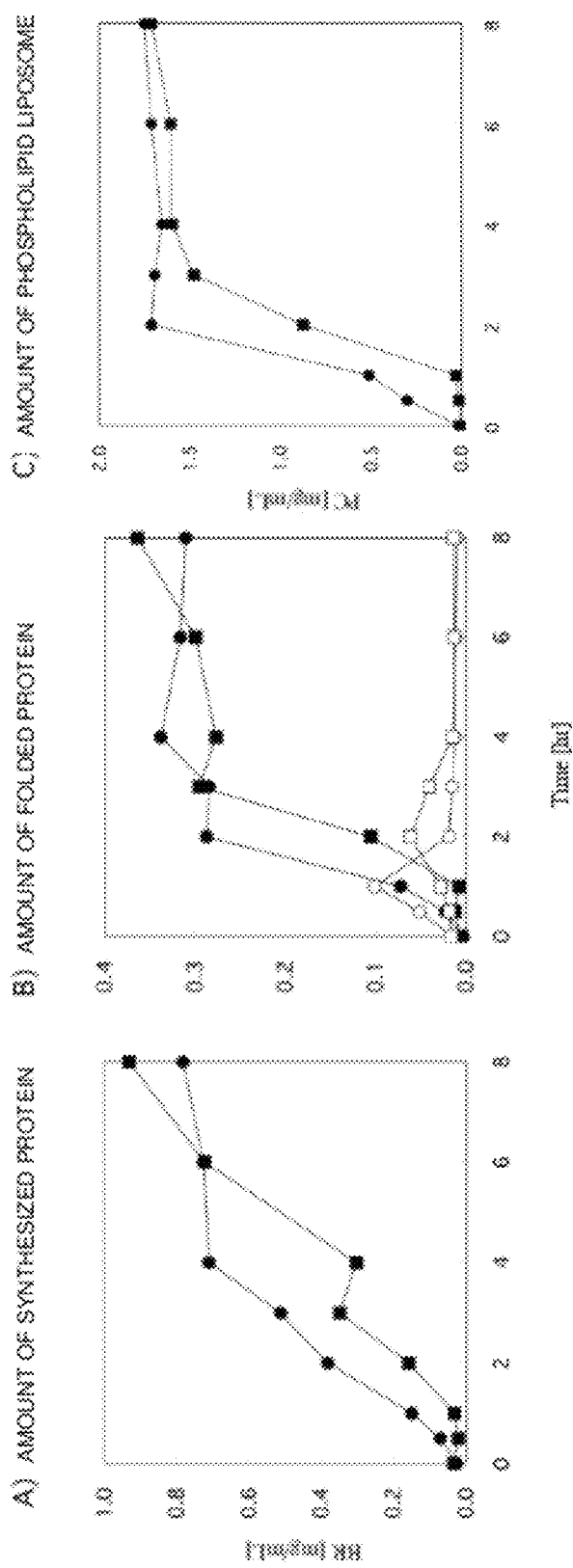
FIGS. 4A-4C show a graphs representing comparison of synthesis speed, production speed of a folded molecule and formation speed of a liposome.

FIG. 4 shows a result obtained from measurement of time change of the amounts of synthesized protein, folded protein, and phospholipid liposome with respect to dialysis time. The amount of synthesized protein was calculated from band intensity of SDS-PAGE/CBB staining. The calculation of the band intensity was conducted using Multi-gauge (Fuji film) and the quantitative determination was performed using high quality purified BR as a control. The amount of folded protein was calculated by visible spectrometry, and the amount of phospholipid liposome was calculated by a colorimetric method with phosphomolybdic acid. In FIG. 4, the circular symbols (○, ●) show a case where 1% (w/v) sodium cholate was added, and the square symbols (□, ■) show a case where 2% (w/v) sodium cholate was added. The hollow symbols ○ and □ show dialysis-time dependency of the amount of an active form in centrifuged supernatant.

In the case of 1% (w/v) cholate, as from 30 min. after initiation of dialysis, the amounts of synthesized protein, folded protein, and phospholipid in centrifuge precipitate are increased (FIG. 4, ● solid circles). Because there is agreement between the speed of generation of folded protein and the speed of formation of phospholipid liposome, it is considered that these two processes proceed cooperatively. In addition, because, after formation of liposome, the amount of synthesized protein increases whereas the amount of folded protein does not increase, it is suggested that the presence of an immature lipid bilayer membrane (lipid disk) contributes to high efficiency of folding, and thus the process of liposome formation is important. Furthermore, because the folded BR appears in centrifuged supernatant so as to peak at 1 hr after initiation of dialysis, it is considered that the folded BR is mainly a molecular species covered with a liposome or lipid disk which is small enough not to be precipitated by centrifugation (FIG. 4(B), ○ hollow circles). In the case of 2% (w/v) cholate, the same phenomena were also observed in all cases because the initiation times were delayed (FIG. 4, ■, □ squares). This means that the concentration of cholate regulates the speeds of the three.

From the foregoing, it is considered that cell-free functional synthesis of a membrane protein is realized via the process as shown in FIG. 5. In the early stage of dialysis, mixed micelle of cholate and lipid is present, which prevents protein synthesis. When the dialysis proceeds and the detergent concentration decreases, lipid disk is formed and protein synthesis is initiated. In the early stage of synthesis, synthesis and folding of polypeptide proceed while its hydrophobic moiety is protected by the lipid disk(s). When the dialysis proceeds further, lipid disks containing the polypeptide are fused to grow to a further large lipid disk or liposome. It is considered that on this occasion folding of membrane protein is promoted using the fusion process of lipid disks.

Example 2

Functional Expression of *E. coli*-Derived Water Channel (AQPZ) in a Cell Free System AQPZ is a six-transmembrane α-helical membrane protein, and serves as a water channel. It is known that AQPZ forms a very stable tetramer.

1) Preparation of AQPZ Synthetic Plasmid

A synthetic plasmid was prepared by amplifying a fragment comprising a native His tag having a recognition site of TEV (Tobacco Etch Virus) (MKDHLIHNVHKEEHAHAHNKDYDIPTTENLYFQGSSG SSG: SEQ ID NO.:1), T7 promoter and T7 terminator by using 2-step PCR, and incorporating the fragment into a pCR2.1 vector. PCR was performed using 5'-primer; 5'-ccagcggctcctcgggaatgttcagaaaattagc-3' (SEQ ID NO.: 5), 3'-primer; 5'-gggcggggat-caatcaatcattaatcacgcttttcca gca-3' (SEQ ID NO.: 6) and *E. coli* colony as a template, and a gene encoding the full-length AQPZ was amplified. Subsequently, with the first PCR product used as a template, second PCR was performed using two chemical synthetic double stranded DNA fragments (5' fragment encoding T7 promoter sequence, N-terminal native His tag, and TEV protease recognition site, and 3' fragment encoding T7 terminator sequence) which partially overlapped with the first PCR product at both terminus regions, and using 5',3'-primer; 5'-gctcttgtcattgtgcttcg-3' (SEQ ID NO.: 4). As a result, a fragment was obtained into which an N-terminal native His tag, and a sequence encoding a protease recognition site, a linker sequence and a full-length AQPZ were inserted between a 5' upstream T7 promoter sequence and a 3' downstream T7 terminator sequence. This fragment was subjected to TA-cloning into pCR2.1-TOPO (Invitrogen) to obtain an AQPZ synthetic plasmid.

2) Confirmation of Integration to a Lipid Bilayer Membrane by Sucrose Density Gradient Centrifugation.

An internal solution of the composition as shown in the above mentioned table 1 was supplied with 9 μg of AQPZ synthetic plasmid, 1% (w/v) sodium cholate, and 6 mg of egg yolk phosphatidylcholine (Type XVI-E, Sigma), the resulting reaction solution of 0.9 ml being poured into a dialysis membrane (Spectra/Por 7, Molecular Weight Cut Off: 15000, Spectrum). The synthesis reaction was conducted at 30° C. for 6 h during dialysis which was performed to 10 times volume (9 mL) of external solution in a 15 mL conical tube by rotary shaking with a rotary shaker (RT-50, TAITEC). After termination of the synthesis reaction, the reaction internal solution was centrifuged at 15000 rpm for 10 min (MX-301, TOMY) to separate into supernatant and precipitate. The precipitate was suspended in 900 μL of PBS, 10 mM EDTA, and ultracentrifuged at 100000×g for 30 min. (CS120GX, Hitachi), and the resulting precipitate was washed. In addition, the precipitate was suspended in 900 μL of 50 mM Tris-HCl (pH 7.0), 400 mM of NaCl, and ultracentrifuged at 100000×g for 30 min. (CS120GX, Hitachi), and the resulting precipitate was washed. This manipulation was conducted twice. The washed precipitate was suspended in 900 μL of 50 mM Tris-HCl (pH 7.0), 400 mM NaCl, and sonicated on ice at 90 W for 30 sec.×3 times (VP-30s, TAITEC). Then centrifugation was performed at 5000 rpm for 5 min. (MX-301, TOMY) to separate into supernatant and precipitate. The centrifuged supernatant was adjusted to 1 mL with 50 mM Tris-HCl (pH 7.0), 400 mM NaCl, and then piled up on 30 (3 mL), 40 (3 mL), 50 (3 mL) % (w/v) solutions for sucrose density gradient as prepared in advance, followed by performing ultracentrifugation with SW41Ti rotor at 100000×g for 10 h (L-80XP, Beckman) to do fractionation from the upper side of the solution by 1 mL. Each fraction was subjected to confirmation of the presence of protein by SDS-PAGE/CBB staining, estimation of the amount of an active form by visible absorbance measurement, and quantitative determination of phospholipid by colorimetric method with phosphomolybdic acid.

Figure 6:
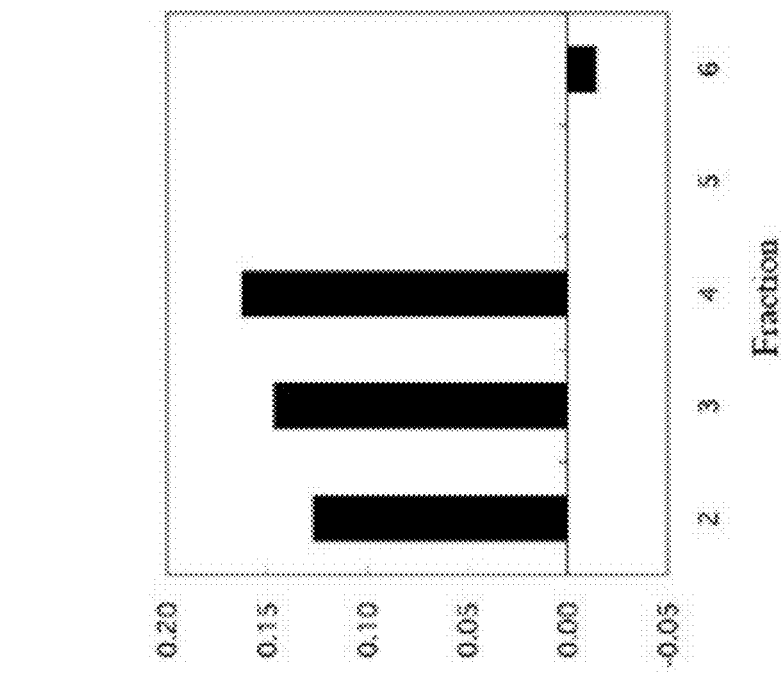
FIG. 6A and FIG. 6B show separation of a cell-free synthesized AQPZ from a liposome by density gradient centrifugation.
Figure 6:
Figure 6:
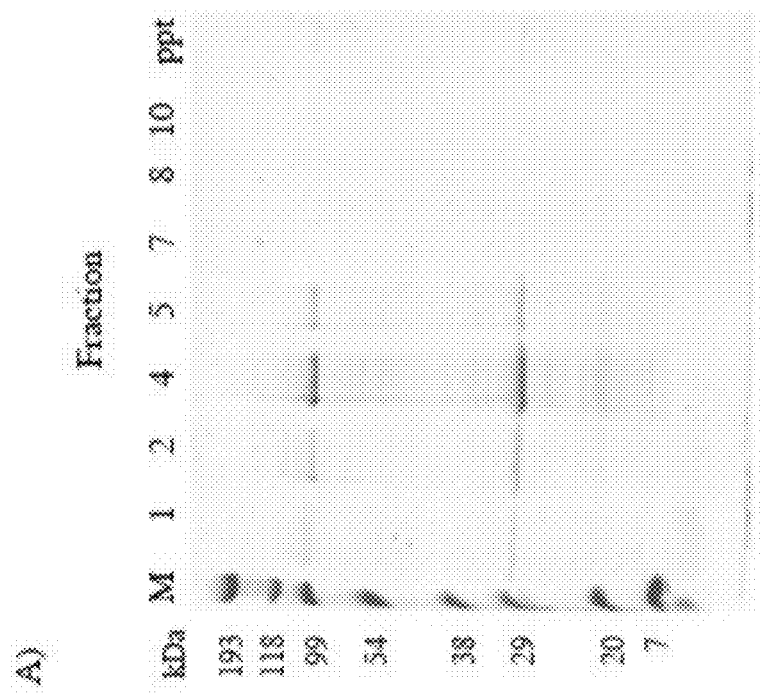

FIG. 6(A) shows a result of SDS-PAGE (XV PANTERA Gel 15%) and CBB staining of 10 μL of each of Fractions 1, 2, 4, 5, 7, 8, 10 and precipitate. As a molecular weight marker (Lane M), 3 μL of Prestained SDS-PAGE Standards Broad Range (Bio-Rad) was subjected to electrophoresis. Detection was performed by CBB staining. FIG. 6(B) shows the amount of phospholipid in Fractions 2-6. From the result as shown in FIG. 6, it was able to be confirmed that the synthesized AQPZ was integrated in a phospholipid liposome, since a protein fraction (FIG. 6(A), Lane 4) and a phospholipid fraction (FIG. 6(B), Lane 4) were present in the same fraction. In addition, it was suggested that the synthesized AQPZ was present also as a molecule of a tetramer form, since a band as derived from AQPZ was detected at around 100 kDa in SDS-PAGE (FIG. 6(A)).

3) Purification of AQPZ

An internal solution of the composition as shown in the above mentioned table 1 was supplied with 45 μg of AQPZ synthetic plasmid, 1% (w/v) sodium cholate, and 30 mg of egg yolk phosphatidylcholine (Type XVI-E, Sigma) to prepare the reaction solution of 4.5 ml, which was then poured into a dialysis membrane (Spectra/Por 7, Molecular Weight Cut Off: 15000, Spectrum). The synthesis reaction was conducted at 30° C. for 6 h during dialysis which was performed to 10 times volume (45 mL) of external solution in a 50 mL conical tube by rotary shaking with a rotary shaker (RT-50, TAITEC). After termination of the synthesis reaction, the reaction internal solution was centrifuged at 15000 rpm for 10 min (MX-301, TOMY) to separate into supernatant and precipitate. The precipitate was suspended in 4 mL of PBS, 10 mM EDTA, and ultracentrifuged at 100000×g for 30 min. (CS120GX, Hitachi), and the resulting precipitate was washed. In addition, the precipitate was suspended in 4 mL of 50 mM Tris-HCl (pH 7.0), 400 mM of NaCl, and ultracentrifuged at 100000×g for 30 min. (CS120GX, Hitachi), and the precipitate was washed. This manipulation was repeated twice. The washed precipitate was suspended in 4 mL of 50 mM Tris-HCl (pH 7.0), 400 mM NaCl, and sonicated on ice at 90 W, for 30 sec.×3 times (VP-30s, TAITEC). Then centrifugation was performed at 5000 rpm for 5 min. (MX-301, TOMY) to separate into supernatant and precipitate. A fraction of 1 mL was taken from the centrifuged supernatant to be subjected to solubilization by mildly agitating at 4° C. for 1 h with 4 mL of solution containing, at final concentration, 50 mM Tris-HCl (pH 7.0), 100 mM NaCl, 10% (v/v) glycerol, 5 mM 2-mercaptoethanol, and 1% (w/v) DDM. The solubilized sample was ultracentrifuged at 100000×g for 1 h (CS120GX, Hitachi) to separate into supernatant and precipitate. The centrifuged supernatant was loaded on HisTrap column (1 mL) (GE Healthcare Bioscience) to do affinity purification. The target protein was eluted using 20 mM Tris-HCl (pH 7.4), 100 mM NaCl, 500 mM imidazole, 0.05% (w/v) DDM, 10% (v/v) glycerol, and 5 mM 2-mercaptoethanol. Fraction of 2.8 mL containing the target protein was concentrated to 200 μL using Amicon Ultra-4 (Molecular Weight Cut Off: 50 k, Millipore). The concentrated sample was loaded on HiLoad 16/60 Superdex 75 pg column (GE Healthcare Bioscience) to do purification by gel filtration. The target protein was eluted using 20 mM Tris-HCl (pH 7.4), 100 mM NaCl, 0.025% (w/v) DDM, 10% (v/v) glycerol, and 2 mM dithiothreitol. A fraction containing the target protein was concentrated to 2.1 mg/mL (total, 60 μL) using Amicon Ultra-4 (Molecular Weight Cut Off: 50 k, Millipore) and Microcon YM-50 (Millipore). The amount of the protein was subjected to quantitative determination by Lowry method using DC Protein Assay kit (Bio-Rad) and BSA as a control.

4) Confirmation of Tetramer Formation by Blue-Native PAGE

Blue-Native PAGE was performed in order to confirm on whether AQPZ as synthesized in the system of the present invention formed a tetramer which is a functional form of AQPZ. The above mentioned purified concentrated sample of 2 μL was supplied with 12 μL of gel filtration buffer (20 mM Tris-HCl (pH 7.4), 100 mM NaCl, 0.025% (w/v) DDM, 10% (v/v) glycerol, 2 mM dithiothreitol, 3 μL of 6× sample buffer (300 mM Bis Tris-HCl (pH 7.0), 60% (v/v) glycerol), and 1 μL of 5% (w/v) CBB-G250, to be applied to NativePage 4-16% Bis-Trisgel (Invitrogen). Dark blue cathode buffer (50 mM BisTris, 50 mM Tricine, 0.02% (w/v) CBB-G250, pH 6.8) as a cathode buffer and 50 mM BisTris, 50 mM Tricine, pH 6.8 as an anode buffer were used to conduct electrophoresis under constant voltage of 150V for 20 min. Then, Dark blue cathode buffer was discarded, and Light blue cathode buffer (50 mM BisTris, 50 mM Tricine, 0.002% (w/v) CBB G-250, pH 6.8) was added instead. Further, electrophoresis was performed under constant voltage of 150V for 40 min., then under constant voltage of 250V for approximately 60 min. The electrophoresis was conducted at 4° C. After termination of the electrophoresis, gel was immersed in destaining solution (20% (v/v) methanol, 10% (v/v) acetic acid) to visualize bands.

Figure 7:
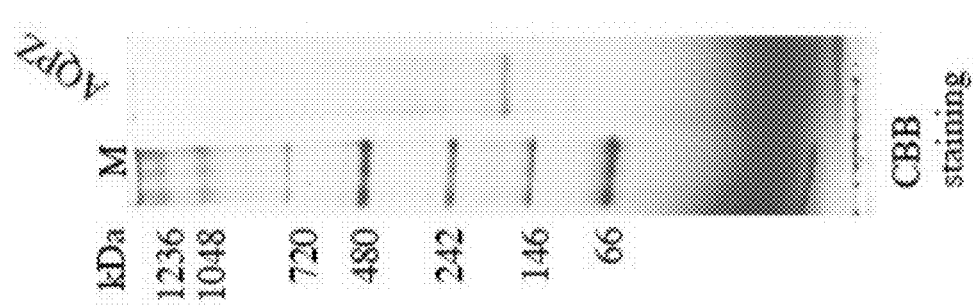
FIG. 7 shows a result of Blue-Native PAGE representing that a cell-free synthesized AQPZ forms a tetramer.

FIG. 7 shows a result of the foregoing. It was able to be confirmed that AQPZ as synthesized in this system of the present invention formed a tetramer also in the presence of DDM, since a clear band was found at around 160 kDa.

Example 3

Functional Expression of *Enterococcus hirae*-Derived V Type ATPase K Subunit (NtpK) in a Cell Free System

*Enterococcus hirae*-derived V type ATPase is a sodium ion pump acting by the energy of ATP hydrolysis, and a supermolecule complex comprising 9 subunits. Among them, K subunit (NtpK) is a 4-transmembrane α-helical membrane protein, constitutes a rotor portion which exists in cell membrane, and forms a ring-shaped decamer.

1) Preparation of NtpK Synthetic Plasmid

A synthetic plasmid was prepared by amplifying a fragment comprising histidine tag having a recognition site of TEV (Tobacco Etch Virus) protease, T7 promoter and T7 terminator by using 2-step PCR, and incorporating the fragment into pCR2.1 vector. A complete synthetic gene as optimized for *E. coli* expression was used as a template. The synthetic gene was provided from Dr. MURATA Takeshi in Kyoto Univ. PCR was performed using 5'-primer; 5'-ccagcggctcctcgggaatgatggattacctgat-3' (SEQ ID NO.: 7) and 3'-primer; 5'-cctgacgagggccccgacgcattcagcaccagcag-3' (SEQ ID NO.: 8), to amplify a gene encoding the full-length NtpK. Subsequently, using the first PCR product used as a template, second PCR was conducted using two chemical synthetic double stranded DNA fragments (5' fragment encoding T7 promoter sequence, and 3' fragment encoding C-terminal 6×His tag and T7 terminator sequence) which partially overlapped with the first PCR product at both terminus regions, and using 5',3'-primer; 5'-gctcttgtcattgtgcttcg-3' (SEQ ID NO.: 4). As a result, a fragment was obtained into which a sequence encoding the full-length NtpK, a linker sequence (SGPSSGENLYFQG: SEQ ID NO.: 9) comprising a TEV protease recognition site, and C-terminal 6×His tag were inserted between a 5' upstream T7 promoter sequence and a 3' downstream T7 terminator sequence. The NtpK synthetic plasmid was obtained by subjecting to TA cloning of this fragment into pCR2.1-TOPO (Invitrogen).

2) Confirmation of Integration to a Lipid Bilayer Membrane by Sucrose Density Gradient Centrifugation An internal solution of the composition as shown in the above mentioned table 1 was supplied with 9 μg of NtpK synthetic plasmid, 1% (w/v) sodium cholate, and 6 mg of egg yolk phosphatidylcholine (Type XVI-E, Sigma) to prepare a reaction solution, 0.9 ml of which was poured into a dialysis membrane (Spectra/Por 7, Molecular Weight Cut Off: 15000, Spectrum). Synthesis reaction was conducted at 30° C. for 6 h during dialysis which was performed to 10 times volume (9 mL) of external solution in a 15 mL conical tube by rotary shaking with a rotary shaker (RT-50, TAITEC). After termination of the synthesis reaction, the reaction internal solution was centrifuged at 15000 rpm for 10 min (MX-301, TOMY) to separate into supernatant and precipitate. The precipitate was suspended in 900 μL of PBS, 10 mM EDTA, and ultracentrifuged at 100000×g for 30 min. (CS120GX, Hitachi). The resulting precipitate was washed. In addition, the precipitate was suspended in 900 μL of 50 mM Tris-HCl (pH 7.0), 400 mM of NaCl, and ultracentrifuged at 100000×g for 30 min. (CS120GX, Hitachi), the resulting precipitate being washed. This manipulation was repeated twice. The washed precipitate was suspended in 900 μL of 50 mM Tris-HCl (pH 7.0), 400 mM NaCl, and sonicated on ice at 90 W for 30 sec.×3 times (VP-30s, TAITEC). Then centrifugation was performed at 5000 rpm for 5 min. (MX-301, TOMY) to separate into supernatant and precipitate. The centrifuged supernatant was adjusted to 1 mL with 50 mM Tris-HCl (pH 7.0), 400 mM NaCl, piled up on 30 (3 mL), 40 (3 mL), 50 (3 mL) % (w/v) solutions for sucrose density gradient as prepared in advance, and ultracentrifuged with SW41Ti rotor at 100000×g for 10 h (L-80XP, Beckman). Fractionation was conducted from the upper side of the resulting solution by 1 mL. Each fraction was subjected to confirmation of the presence of protein by SDS-PAGE/CBB staining, estimation of the amount of an active form by visible absorbance measurement, and quantitative determination of phospholipid by a colorimetric method with phosphomolybdic acid.

Figure 8:
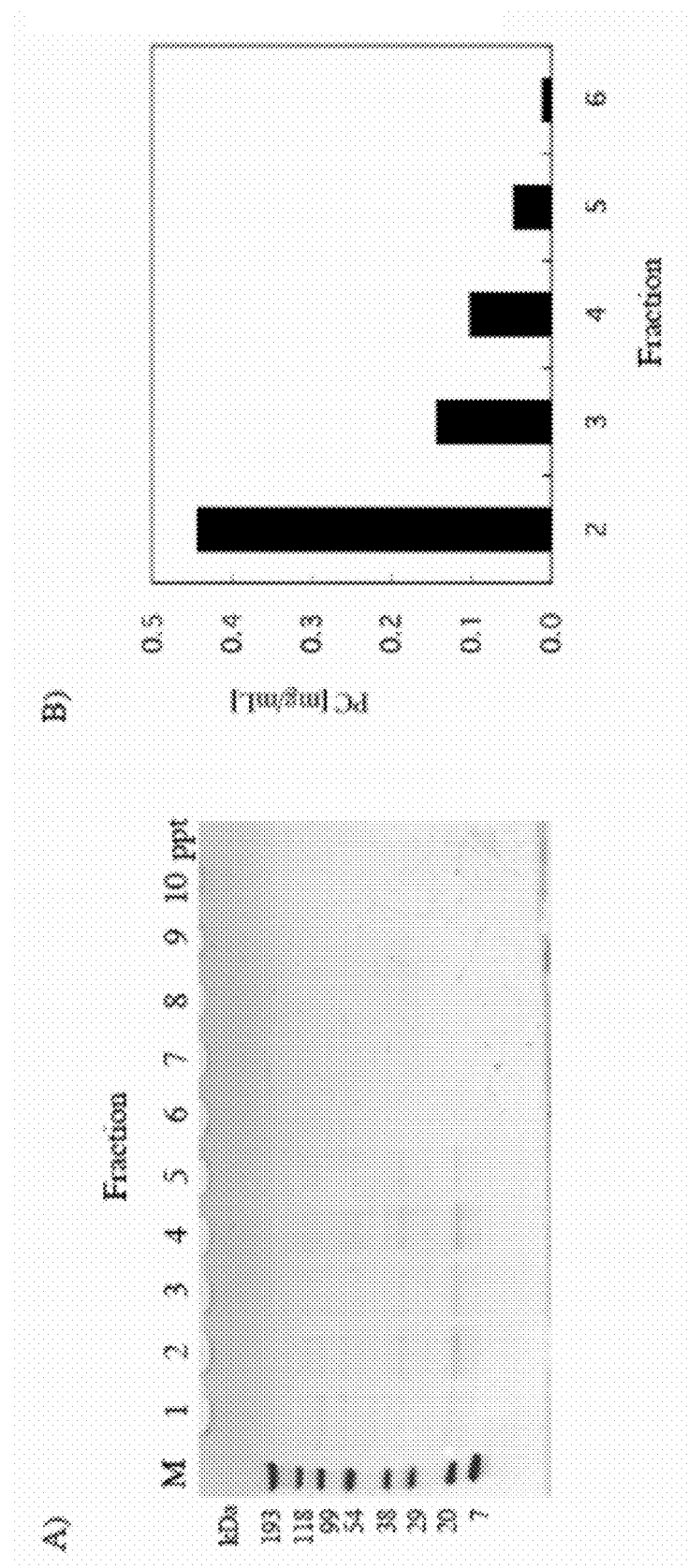
FIG. 8A and FIG. 8B show separation of a cell-free synthesized NtpK from a liposome by density gradient centrifugation.

FIG. 8(A) shows a result of SDS-PAGE analysis of 10 μL of each of fractions and precipitate, and FIG. 8(B) shows a result of the amounts of phospholipid in Fractions 2-6. From the results, it is suggested that the synthesized NtpK was integrated in a phospholipid liposome, since also phospholipid was present (FIG. 8(B), Lane 4) in the fraction (FIG. 8(A), Lane 4) where proteins were present abundantly.

3) Purification of NtpK

An internal solution of the composition as shown in the above mentioned table 1 was supplied with 45 μg of NtpK synthetic plasmid, 1% (w/v) sodium cholate, and 30 mg of egg yolk phosphatidylcholine (Type XVI-E, Sigma) to prepare 4.5 ml of the reaction solution, which was poured into a dialysis membrane (Spectra/Por 7, Molecular Weight Cut Off: 15000, Spectrum). The synthesis reaction was conducted at 30° C. for 6 h during dialysis which was performed to 10 times volume (45 mL) of external solution in a 50 mL conical tube by rotary shaking with a rotary shaker (RT-50, TAITEC). After termination of the synthesis reaction, the reaction internal solution was centrifuged at 15000 rpm for 10 min (MX-301, TOMY) to separate into supernatant and precipitate. The precipitate was suspended in 2 mL of PBS, 10 mM EDTA, and ultracentrifuged at 100000×g for 30 min. (CS120GX, Hitachi). The resulting precipitate was washed. In addition, the precipitate was suspended in 2 mL of 50 mM Tris-HCl (pH 7.0), 400 mM of NaCl, and ultracentrifuged at 100000×g for 30 min. (CS120GX, Hitachi), the resulting precipitate being washed. This manipulation was repeated twice. Half of the washed precipitate was suspended in 1 mL of 50 mM Tris-HCl (pH 7.0), 400 mM NaCl, and sonicated on ice at 90 W for 30 sec.×3 times (VP-30s, TAITEC). Then centrifugation was performed at 5000 rpm for 5 min. (MX-301, TOMY) to separate into supernatant and precipitate. A fraction of 1 mL was taken from the centrifuged supernatant to be subjected to solubilization by mildly agitating at 4° C. for 1 h in 4 mL of solution containing, at final concentration, 50 mM Tris-HCl (pH 7.0), 100 mM NaCl, 20% (v/v) glycerol and 1% (w/v) DDM. The solubilized sample was ultracentrifuged at 100000×g for 1 h (CS120GX, Hitachi) to separate into supernatant and precipitate. The centrifuged supernatant was loaded on HisTrap column (1 mL) (GE Healthcare Bioscience) to do affinity purification. The target protein was eluted using 20 mM Tris-HCl (pH 7.4), 10 mM NaCl, 500 mM imidazole, 0.05% (w/v) DDM, and 20% (v/v) glycerol. A fraction of 2.8 mL containing the target protein was concentrated to 500 µL using Amicon Ultra-4 (Molecular Weight Cut Off: 50 k, Millipore). The concentrated sample was loaded on Superdex 200 10/300 GL column (GE Healthcare Bioscience) to do purification by gel filtration. The target protein was eluted using 20 mM Tris-HCl (pH 7.4), 10 mM NaCl, 0.05% (w/v) DDM, and 20% (v/v) glycerol. A fraction containing the target protein was concentrated to 0.7 mg/mL (total, 100 µL) using Amicon Ultra-4 (Molecular Weight Cut Off: 50 k, Millipore). The amount of the protein was quantitated by Lowry method using DC Protein Assay kit (Bio-Rad) and BSA as a control.

4) Confirmation of Decamer Formation by Blue-Native PAGE

Blue-Native PAGE was performed in order to confirm on whether NtpK synthesized in the system of the present invention formed a decamer ring which is a functional form thereof. The above mentioned gel-filtrated purified sample of 14 µL was supplied with 3 µL of 6× sample buffer (300 mM Bis-Tris-HCl (pH 7.0), 60% glycerol), 1 µL of 5% (w/v) CBB-G250, to be applied to NativePAGE 4-16% Bis-Tris gel (Invitrogen). Dark blue cathode buffer (50 mM BisTris, 50 mM Tricine, 0.02% (w/v) CBB G-250, pH 6.8) as a cathode buffer and 50 mM BisTris, 50 mM Tricine, pH 6.8 as an anode buffer were used to do electrophoresis under constant voltage of 150V for 20 min., and then Dark blue cathode buffer was discarded and added with Light blue cathode buffer (50 mM BisTris, 50 mM Tricine, 0.002% (w/v) CBB G-250, pH 6.8) instead. Further electrophoresis was conducted under constant voltage of 150V for 40 min., then under constant voltage of 250V for approximately 60 min. The electrophoresis was done at 4° C. After termination of the electrophoresis, the gel was immersed in destaining solution (20% (v/v) methanol, 10% (v/v) acetic acid) to visualize bands. In addition, the destained gel was subjected to silver staining by a silver staining reagent "Daiich" (Daiichi Pure Chemicals).

Figure 9:
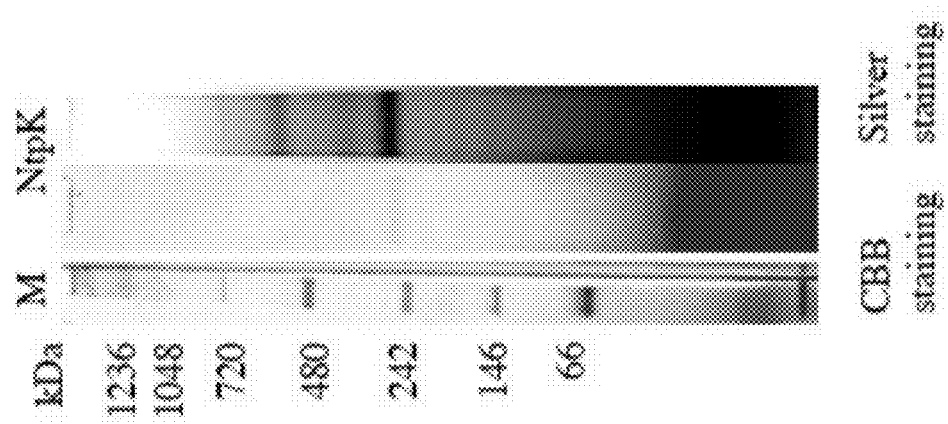
FIG. 9 shows a result of Blue-Native PAGE representing that cell-free synthesized NtpK forms decamer.

FIG. 9 shows a result of the forgoing. It has been suggested that NtpK as synthesized in the system of the present invention formed a decamer ring also in the presence of DDM, since a clear band is found at around 245 kDa.

Example 4

Functional Expression of a Group of Multiple Transmembrane Membrane Proteins Having Various Properties In order to confirm integration into a lipid bilayer membrane, 30, 40, 50% sucrose density gradient centrifugation was performed for samples of E. coli multidrug efflux transporter EmrE (4-transmembrane type), Human tight junction protein Cldn4 (4-transmembrane type), G protein-coupled receptor Human adrenaline receptor (β2AR), and Human muscarine receptor (m2AChR) (7-transmembrane type) which were synthesized in cell free system in the co-existence of 1% sodium cholate/6 mg egg yolk phosphatidylcholine or E. coli lipid according to the above mentioned method.

1) Preparation of a Synthetic Plasmid

A synthetic plasmid was prepared by amplifying a fragment comprising a native his tag having a recognition site of TEV protease (MKDHLIHNVHKEEHAHAHNKDYDIPT-TENLYFQGSSGSSG: SEQ ID NO.: 1), T7 promoter and T7 terminator by using 2-step PCR, and incorporating the fragment into pCR2.1 vector. Amplification of a gene encoding the full-length EmrE was performed by PCR using 5'-primer; 5'-ccagcggctcctcgggaatgaacccttatattta-3' (SEQ ID NO.: 10), 3'-primer; 5'-gggcggggatcaatcaatcattaatgtggtgtgcttcgtg-3' (SEQ ID NO.: 11), and, as a template, E. coli genome as prepared by standard method. Amplification of a gene encoding the full-length Cldn4 was performed by PCR using 5'-primer; 5'-ccagcggctcctcgggaatggcctccatgggggct-3' (SEQ ID NO.: 12), 3'-primer; 5'-gggcggggatcaatcaatcattacacg-tagttgctg gca-3' (SEQ ID NO.: 13), and, as a template, a clone as provided from "Full-length Human cDNA Sequencing Analysis" project. Subsequently, using the above mentioned first PCR product used as a template, second PCR was conducted using two chemical synthetic double stranded DNA fragments (5' fragment encoding T7 promoter sequence and N-terminal native His tag, and 3' fragment encoding T7 terminator sequence) which partially overlapped with the first PCR product at both terminus regions, and using 5',3'-primer; 5'-gctcttgtcattgtgcttcg-3' (SEQ ID NO.: 4). As a result, a fragment was obtained into which a sequence encoding N-terminal native His tag, TEV protease recognition site, the full-length target protein was inserted between a 5' upstream T7 promoter sequence and a 3' downstream T7 terminator sequence. This fragment was subjected to TA cloning into pCR2.1-TOPO (Invitrogen) to obtain a synthetic plasmid.

Amplification of a gene encoding the full-length β2AR was performed by PCR using 5'-primer; 5'-tccagcggctcctcgg-gaatggggcaaccc ggg-3' (SEQ ID NO.: 14), 3'-primer; 5'-cct-gacgagggccccgacagcagtgagtc atttgta-3' (SEQ ID NO.: 15), and, as a template, a protein expression vector for β2AR E. coli in a cell free system (see Non-Patent Document 1). Amplification of a gene encoding the full-length m2AChR was performed by PCR using 5'-primer; 5'-tccagcggctcctcgg-gaatggatgactc cacgga-3' (SEQ ID NO.: 16), 3'-primer; 5'-cct-gacgagggccccgaccttgtag cgcctatgt-3' (SEQ ID NO.: 17), and, as a template, a protein expression vector for 2 mAChR E. coli in a cell free system (see Non-Patent Document 1).

Subsequently, with the above mentioned first PCR product used as a template, second PCR was conducted using two chemical synthetic double stranded DNA fragments (5' fragment encoding T7 promoter sequence, N-terminal native His tag, and TEV protease recognition site and 3' fragment encoding T7 terminator sequence and C-terminal linker sequence) which partially overlapped with the first PCR product at both terminus regions, and using 5', 3' primer; 5'-gctcttgtcattgtgct-tcg-3' (SEQ ID NO.: 4). As a result, a fragment was obtained into which a sequence encoding N-terminal native His tag, TEV protease recognition site, a sequence encoding the full-length target protein, and C-terminal linker sequence (SGPSSG: SEQ ID NO.: 18) were inserted between a 5' upstream T7 promoter sequence and a 3' downstream T7 terminator sequence. This fragment was subjected to TA cloning into pCR2.1-TOPO (Invitrogen) to obtain a synthetic plasmid.

2) Confirmation of Integration to a Lipid Bilayer Membrane by Sucrose Density Gradient Centrifugation An internal solution of the composition as shown in the above mentioned table 1 was supplied with 9 µg of the target protein synthetic plasmid, 1% (w/v) sodium cholate, and 6 mg of egg yolk phosphatidylcholine (Type XVI-E, Sigma) or *E. coli* lipid (Avanti), to prepare a reaction solution, 0.9 ml of which was then poured into a dialysis membrane (Spectra/Por 7, Molecular Weight Cut Off: 15000, Spectrum). A synthesis reaction was conducted at 30° C. for 6 h during dialysis which was performed to 10 times volume (9 mL) of external solution in a 15 mL conical tube by rotary shaking with a rotary shaker (RT-50, TAITEC). After termination of the synthesis reaction, the reaction internal solution was centrifuged at 15000 rpm for 10 min (MX-301, TOMY) to separate into supernatant and precipitate. The precipitate was suspended in 900 µL of PBS, 10 mM EDTA and ultracentrifuged at 100000×g for 30 min. (CS120GX, Hitachi), the resulting precipitate being washed. In addition, the precipitate was suspended in 900 µL of 50 mM Tris-HCl (pH 7.0), 400 mM of NaCl and ultracentrifuged at 100000×g for 30 min. (CS120GX, Hitachi), the resulting precipitate being washed. This manipulation was repeated twice. The washed precipitate was suspended in 900 µL of 50 mM Tris-HCl (pH 7.0), 400 mM NaCl, and sonicated on ice at 90 W for 30 sec.×3 times (VP-30s, TAITEC). Then centrifugation was performed at 5000 rpm for 5 min. (MX-301, TOMY) to separate into supernatant and precipitate. The centrifuged supernatant was adjusted to 1 mL with 50 mM Tris-HCl (pH 7.0), 400 mM NaCl, piled up on 30 (3 mL), 40 (3 mL), 50 (3 mL) % (w/v) solution for sucrose density gradient as prepared in advance, and ultracentrifuged with SW41Ti rotor at 100000×g for 10 h (L-80XP, Beckman). Fractionation was conducted from the upper side of the resulting solution by 1 mL. Each fraction was subjected to confirmation of the presence of protein by SDS-PAGE/CBB staining, and quantitative determination of phospholipid by colorimetric method with phosphomolybdic acid.

Figure 10:
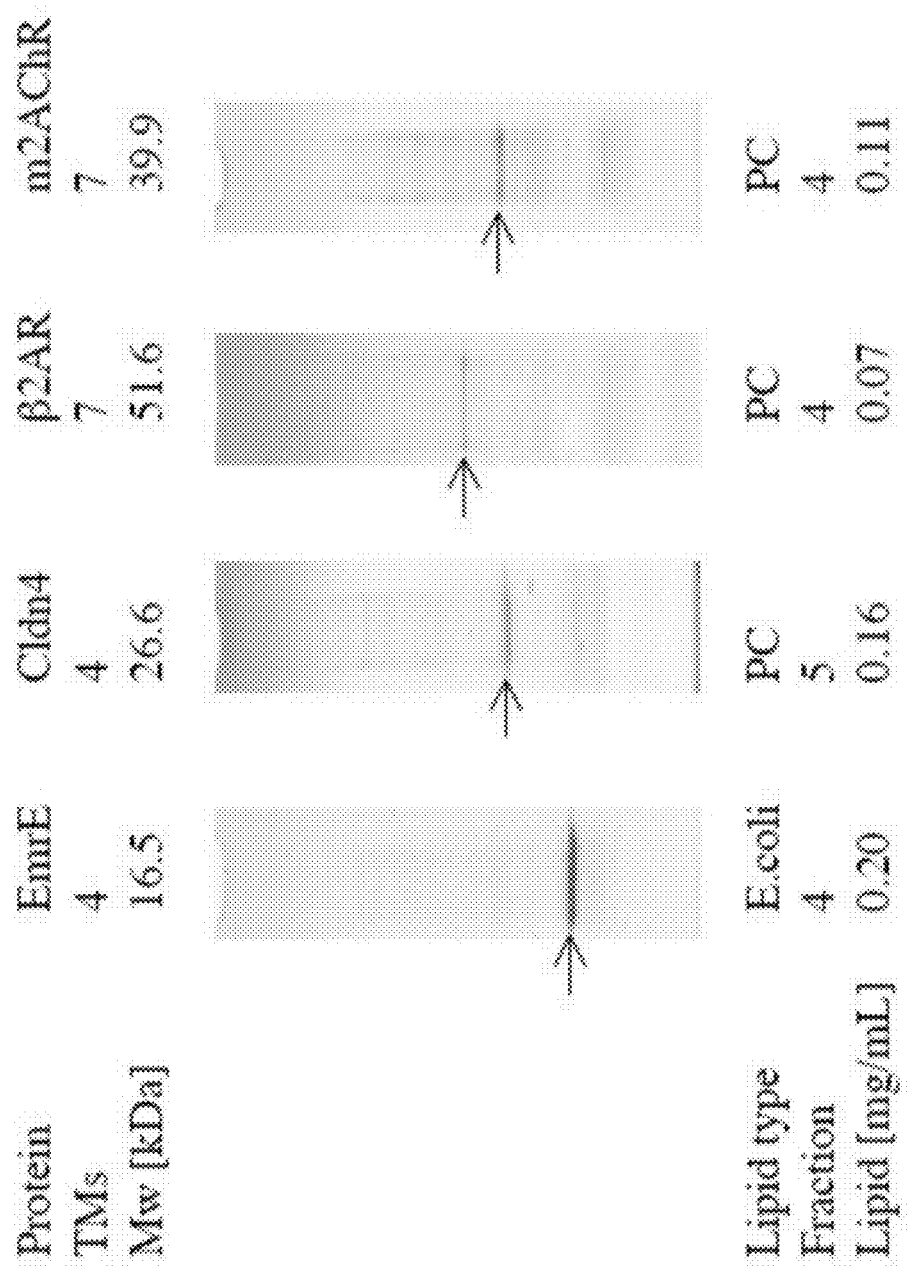
FIG. 10 shows a result representing synthesis of various membrane proteins and integration thereof into liposome.

FIG. 10 shows a result of the foregoing. The samples of *E. coli* multidrug efflux transporter EmrE (4-transmembrane type), Human tight junction protein Cldn4 (4-transmembrane type), G protein-coupled receptor Human adrenaline receptor (β2AR), and Human muscarine receptor (m2AChR) (7-transmembrane type) which were synthesized in cell free system in the co-existence of 1% (w/v) sodium cholate/6 mg egg yolk phosphatidylcholine or *E. coli* lipid were subjected to 30, 40, 50% sucrose density gradient centrifugation, and fractionation was conducted from the upper side of the resulting solution by 1 mL. FIG. 10 shows a result of SDS-PAGE and CBB staining which was performed for 10 µL of fraction as represented in FIG. 10, and phospholipid contents. EmrE was synthesized in the co-existence of 1% (w/v) sodium cholate/6 mg *E. coli* lipid in a cell free system. The other proteins than EmrE were synthesized in the co-existence of 1% (w/v) sodium cholate/6 mg of egg yolk phosphatidylcholine in a cell free system. Molecular weights as represented in FIG. 10 all include that of N-terminal native His tag. From those results, it has been confirmed that the synthesized membrane proteins are all integrated in a phospholipid liposome, since a phospholipid is present also in fractions where the proteins are present.

Here, it is to be noted that the disclosures of the above mentioned Patent Documents etc. are all incorporated herein in their entireties by reference thereto. It should be noted that changes and modifications of the modes or Examples may be done within the entire disclosure (inclusive of the claims) of the present invention and on the basis of the basic technical spirits thereof. Also, it should be noted that a variety of combinations or selections of various elements as disclosed may be made within the scope of the claims of the present invention. That is, it should be noted that the present invention also includes various changes and modifications which can be made by a person skilled in the art on the basis of all the disclosure (inclusive of the claims) and technical spirits.

The invention claimed is:

1. A method for producing a membrane protein folded to its native or active structure in a lipid disk or liposome, comprising:
   (a) preparing a reaction solution for cell-free protein synthesis containing a polynucleotide encoding a membrane protein, a steroidal detergent, and a phospholipid, wherein the steroidal detergent is contained at a concentration higher than its critical micelle concentration,
   (b) decreasing the concentration of said steroidal detergent in the reaction solution, and
   (c) synthesizing the membrane protein simultaneously with formation of a lipid disk or liposome into which the synthesized membrane protein is integrated.

2. The method of claim 1, wherein said membrane protein is synthesized by a cell-free protein synthesis reaction using a dialysis method, and said steroidal detergent is contained in the reaction solution at an initial concentration of 1.5 to 10 times higher than its critical micelle concentration.

3. The method of claim 1, wherein said steroidal detergent is digitonin, cholate or CHAPS.

4. The method of claim 1, wherein said reaction solution for cell-free protein synthesis contains 10 to 20 mg/ml sodium cholate at an initial concentration.

5. The method of claim 1, wherein said reaction solution for cell-free protein synthesis contains 5 to 10 mg/mL CHAPS at an initial concentration.

6. The method of claim 1, wherein said reaction solution for cell-free protein synthesis contains 1 to 4 mg/mL digitonin at an initial concentration.

7. The method of claim 1, wherein said (b) comprises adsorbing the detergent by using a resin capable of binding to the detergent.

8. The method of claim 1, wherein the membrane protein comprises a receptor protein, a channel protein, a transporter, a membrane-bound enzyme, or a partial sequence, a homologous sequence, a modified sequence and an inducible sequence thereof.

9. The method of claim 1, further comprising a step of solubilizing the membrane protein from the resultant complex with the lipid disk or liposome to purify the membrane protein.

10. A composition for screening a pharmaceutical agent, the composition comprising the membrane protein produced by the method of claim 1, the protein being in a state of being integrated into a lipid disk or liposome.

* * * * *

SEQUENCE LISTING

```
<160> NUMBER OF SEQ ID NOS: 18

<210> SEQ ID NO 1
<211> LENGTH: 40
<212> TYPE: PRT
<213> ORGANISM: Artificial Sequence
<220> FEATURE:
<223> OTHER INFORMATION: Native his-tag

<400> SEQUENCE: 1

Met Lys Asp His Leu Ile His Asn Val His Lys Glu Glu His Ala His
1               5                   10                  15

Ala His Asn Lys Asp Tyr Asp Ile Pro Thr Thr Glu Asn Leu Tyr Phe
            20                  25                  30

Gln Gly Ser Ser Gly Ser Ser Gly
        35                  40

<210> SEQ ID NO 2
<211> LENGTH: 33
<212> TYPE: DNA
<213> ORGANISM: Artificial Sequence
<220> FEATURE:
<223> OTHER INFORMATION: 5' primer for BR

<400> SEQUENCE: 2
```

```
tccagcggct cctcgggaca ggcccagatc acc                                    33
```

<210> SEQ ID NO 3
<211> LENGTH: 39
<212> TYPE: DNA
<213> ORGANISM: Artificial Sequence
<220> FEATURE:
<223> OTHER INFORMATION: 3' primer for BR

<400> SEQUENCE: 3

```
gggcggggat caatcaatca ttatcagtcg ctggtcgcg                              39
```

<210> SEQ ID NO 4
<211> LENGTH: 20
<212> TYPE: DNA
<213> ORGANISM: Artificial Sequence
<220> FEATURE:
<223> OTHER INFORMATION: 5', 3' primer

<400> SEQUENCE: 4

```
gctcttgtca ttgtgcttcg                                                   20
```

<210> SEQ ID NO 5
<211> LENGTH: 34
<212> TYPE: DNA
<213> ORGANISM: Artificial Sequence
<220> FEATURE:
<223> OTHER INFORMATION: 5' primer for AQPZ

<400> SEQUENCE: 5

```
ccagcggctc ctcgggaatg ttcagaaaat tagc                                   34
```

<210> SEQ ID NO 6
<211> LENGTH: 40
<212> TYPE: DNA
<213> ORGANISM: Artificial Sequence
<220> FEATURE:
<223> OTHER INFORMATION: 3' primer for AQPZ

<400> SEQUENCE: 6

```
gggcggggat caatcaatca ttaatcacgc ttttccagca                             40
```

<210> SEQ ID NO 7
<211> LENGTH: 34
<212> TYPE: DNA
<213> ORGANISM: Artificial Sequence
<220> FEATURE:
<223> OTHER INFORMATION: 5' primer for NtpK

<400> SEQUENCE: 7

```
ccagcggctc ctcgggaatg atggattacc tgat                                   34
```

<210> SEQ ID NO 8
<211> LENGTH: 35
<212> TYPE: DNA
<213> ORGANISM: Artificial Sequence
<220> FEATURE:
<223> OTHER INFORMATION: 3' primer for NtpK

<400> SEQUENCE: 8

```
cctgacgagg gccccgacgc attcagcacc agcag                                  35
```

<210> SEQ ID NO 9
<211> LENGTH: 13
<212> TYPE: PRT
<213> ORGANISM: Artificial Sequence
<220> FEATURE:

<223> OTHER INFORMATION: Recognition site for TEV protease

<400> SEQUENCE: 9

Ser Gly Pro Ser Ser Gly Glu Asn Leu Tyr Phe Gln Gly
1               5                   10

<210> SEQ ID NO 10
<211> LENGTH: 34
<212> TYPE: DNA
<213> ORGANISM: Artificial Sequence
<220> FEATURE:
<223> OTHER INFORMATION: 5' primer for EmrE

<400> SEQUENCE: 10
ccagcggctc ctcgggaatg aacccttata ttta                          34

<210> SEQ ID NO 11
<211> LENGTH: 40
<212> TYPE: DNA
<213> ORGANISM: Artificial Sequence
<220> FEATURE:
<223> OTHER INFORMATION: 3' primer for EmrE

<400> SEQUENCE: 11
gggcggggat caatcaatca ttaatgtggt gtgcttcgtg                    40

<210> SEQ ID NO 12
<211> LENGTH: 34
<212> TYPE: DNA
<213> ORGANISM: Artificial Sequence
<220> FEATURE:
<223> OTHER INFORMATION: 5' primer for Cldn4

<400> SEQUENCE: 12
ccagcggctc ctcgggaatg gcctccatgg ggct                          34

<210> SEQ ID NO 13
<211> LENGTH: 39
<212> TYPE: DNA
<213> ORGANISM: Artificial Sequence
<220> FEATURE:
<223> OTHER INFORMATION: 3' primer for Cldn4

<400> SEQUENCE: 13
gggcggggat caatcaatca ttacacgtag ttgctggca                     39

<210> SEQ ID NO 14
<211> LENGTH: 33
<212> TYPE: DNA
<213> ORGANISM: Artificial Sequence
<220> FEATURE:
<223> OTHER INFORMATION: 5' primer for beta-2AR

<400> SEQUENCE: 14
tccagcggct cctcgggaat ggggcaaccc ggg                           33

<210> SEQ ID NO 15
<211> LENGTH: 36
<212> TYPE: DNA
<213> ORGANISM: Artificial Sequence
<220> FEATURE:
<223> OTHER INFORMATION: 3' primer for beta-2AR

<400> SEQUENCE: 15
cctgacgagg gccccgacag cagtgagtca tttgta                        36

```
<210> SEQ ID NO 16
<211> LENGTH: 35
<212> TYPE: DNA
<213> ORGANISM: Artificial Sequence
<220> FEATURE:
<223> OTHER INFORMATION: 5' primer for m2AchR

<400> SEQUENCE: 16
tccagcggct cctcgggaat ggatgactcc acgga                              35

<210> SEQ ID NO 17
<211> LENGTH: 34
<212> TYPE: DNA
<213> ORGANISM: Artificial Sequence
<220> FEATURE:
<223> OTHER INFORMATION: 3' primer for m2AchR

<400> SEQUENCE: 17
cctgacgagg gccccgacct tgtagcgcct atgt                               34

<210> SEQ ID NO 18
<211> LENGTH: 6
<212> TYPE: PRT
<213> ORGANISM: Artificial Sequence
<220> FEATURE:
<223> OTHER INFORMATION: C-terminal linker

<400> SEQUENCE: 18

Ser Gly Pro Ser Ser Gly
1               5
```